(12) United States Patent
Utku

(10) Patent No.: US 9,399,679 B2
(45) Date of Patent: Jul. 26, 2016

(54) THERAPEUTIC ANTI-TIRC7 ANTIBODIES FOR USE IN IMMUNE RELATED AND OTHER DISEASES

(71) Applicant: Nalan Utku, Berlin (DE)

(72) Inventor: Nalan Utku, Berlin (DE)

( * ) Notice: Subject to any disclaimer, the term of this patent is extended or adjusted under 35 U.S.C. 154(b) by 497 days.

(21) Appl. No.: 13/725,535

(22) Filed: Dec. 21, 2012

(65) Prior Publication Data

US 2013/0323254 A1 Dec. 5, 2013

Related U.S. Application Data

(63) Continuation of application No. 13/458,981, filed on Apr. 27, 2012, now abandoned, which is a continuation of application No. 13/233,867, filed on Sep. 15, 2011, now abandoned, which is a continuation of application No. 10/513,539, filed as application No. PCT/EP02/14734 on Dec. 23, 2002, now abandoned.

(30) Foreign Application Priority Data

Dec. 21, 2001 (EP) .................... 01130730

(51) Int. Cl.
  *A61K 39/395* (2006.01)
  *C07K 16/28* (2006.01)
  *A61K 45/06* (2006.01)
  *C07K 7/00* (2006.01)
  *C07K 14/00* (2006.01)
  *A61K 39/00* (2006.01)

(52) U.S. Cl.
  CPC ....... *C07K 16/2803* (2013.01); *A61K 39/39541* (2013.01); *A61K 45/06* (2013.01); *C07K 7/00* (2013.01); *C07K 14/00* (2013.01); *C07K 16/28* (2013.01); *A61K 2039/505* (2013.01); *C07K 2317/24* (2013.01)

(58) Field of Classification Search
  None
  See application file for complete search history.

(56) References Cited

U.S. PATENT DOCUMENTS

| | | |
|---|---|---|
| 7,794,715 B2 | 9/2010 | Utku |
| 2005/0048067 A1 | 3/2005 | Utku |
| 2005/0220789 A1 | 10/2005 | Utku et al. |
| 2006/0251646 A1 | 11/2006 | Utku |
| 2006/0292143 A1 | 12/2006 | Utku et al. |
| 2011/0189181 A1 | 8/2011 | Utku et al. |

FOREIGN PATENT DOCUMENTS

| | | |
|---|---|---|
| DE | 197 38 710 A | 3/1999 |
| WO | WO 99/11782 | 3/1999 |
| WO | WO 03/025000 A2 | 3/2003 |

OTHER PUBLICATIONS

Van den Beucken et al., J Mol Biol. Jul. 13, 2001;310(3):591-601.*
Cassett, Florence et al., "A peptide mimetic of an anti-CD4 monoclonal antibody by rational design," *Biochemical and Biophysical Research Communications*, 2003, vol. 307, Issue 1, p. 198-205.
Huang, Ziwei, "Structural chemistry and therapeutic intervention of protein-protein interactions in immune response, human immunodeficiency virus entry, and apoptosis," *Pharmacology & Therapeutics*, Jun. 2000, vol. 86, No. 3, p. 201-215.
Portolano, Stefano et al., "Lack of Promiscuity in Autoantigen-Specific H and L Chain Combinations as Revealed by Human H and L Chain "Roulette"1," *The Journal of Immunology*, Feb. 1, 1993, vol. 150, No. 3, p. 880-887.
Skerra, Arne, "Engineered protein scaffolds for molecular recognition," *Journal of Molecular Recognition*, 2000, vol. 13, p. 167-187.
Utku, Nalan, et al., "Prevention of Acute Allograft Rejection by Antibody Targeting of TIRC7, a Novel T Cell Membrane Protein," *Immunity*, Oct. 1998, vol. 9, p. 509-518.

* cited by examiner

*Primary Examiner* — Zachary Skelding
(74) *Attorney, Agent, or Firm* — Saliwanchik, Lloyd & Eisenschenk

(57) ABSTRACT

Provided are specific antibodies against T-cell immune response cDNA7 (TIRC7) costimulatory molecule, which are capable of inhibiting proliferation of peripheral blood mononuclear cells (PBMCs). In particular, high affinity monoclonal and chimeric anti-TIRC7 antibodies are described. Compositions comprising such antibodies and their use for the treatment of immune diseases are provided.

12 Claims, 9 Drawing Sheets

Figure 1:
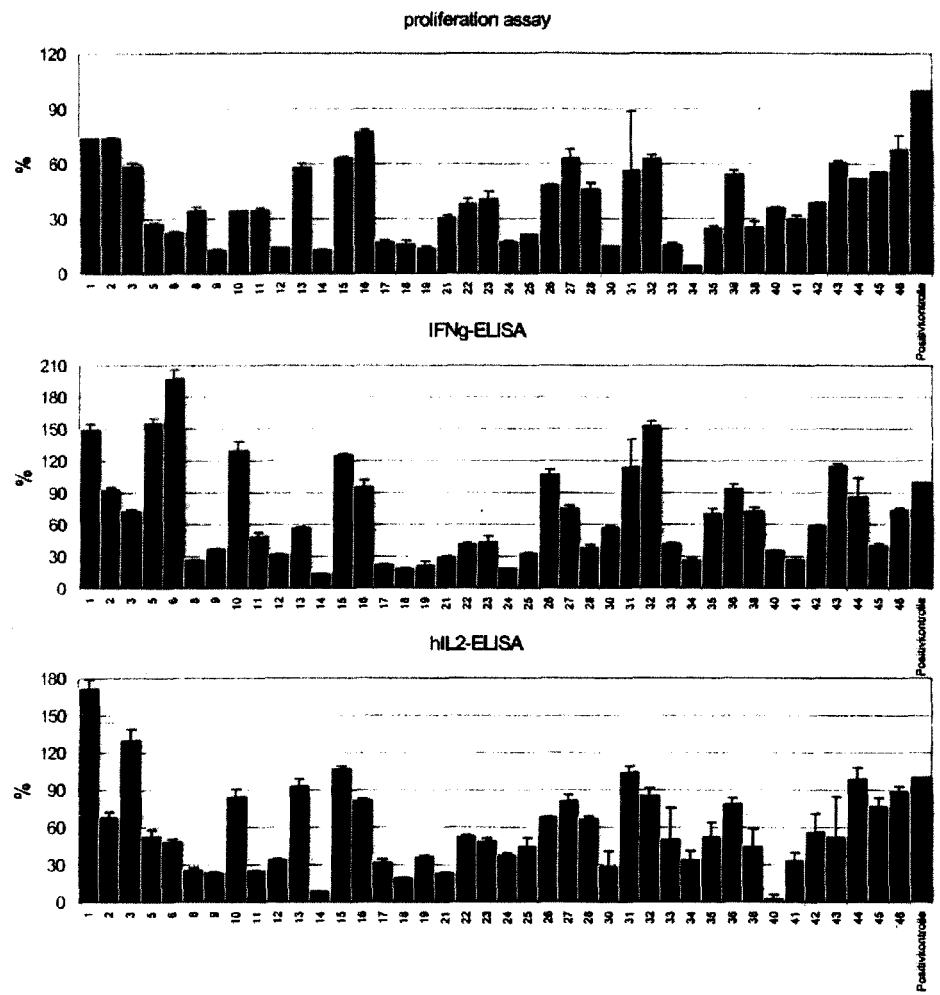

Applicant: Nalan Utku
U.S. Serial No.: Not Yet Known
(continuation of U.S. Serial No.
13/458,981, filed April 27, 2012)
Filed: Herewith
Exhibit A

```
          10         20         30         40         50         60
           *          *          *          *          *          *
GAGGTGCAGCTGCAACAGTCTGGACCTGAGCTGGTAAAGCCTGGGGCTTCAGTGAAGATG
CTCCACGTCGACGTTGTCAGACCTGGACTCGACCATTTCGGACCCCGAAGTCACTTCTAC
 E   V   Q   L   Q   Q   S   G   P   E   L   V   K   P   G   A   S   V   K   M>

70         80         90        100        110        120
           *          *          *          *          *          *
TCCTGCAAGGCTTCTGGATACACATTCACTAGCTATGTTATACACTGGGTGAAACAGAAG
AGGACGTTCCGAAGACCTATGTGTAAGTGATCGATACAATATGTGACCCACTTTGTCTTC
 S   C   K   A   S   G   Y   T   F   T   S   Y   V   I   H   W   V   K   Q   K>

130        140        150        160        170        180
           *          *          *          *          *          *
CCTGGGCAGGGCCTTGAGTGGATTGGATATATTAATCCTTACAACTATGATACTAAATAC
GGACCCGTCCCGGAACTCACCTAACCTATATAATTAGGAATGTTGATACTATGATTTATG
 P   G   Q   G   L   E   W   I   G   Y   I   N   P   Y   N   Y   D   T   K   Y>

190        200        210        220        230        240
           *          *          *          *          *          *
AATGAGAAGTTCAAAGGCGAGGCCACACTGACTTCAGACAAATCCTCCAATACAGCCTAC
TTACTCTTCAAGTTTCCGCTCCGGTGTGACTGAAGTCTGTTTAGGAGGTTATGTCGGATG
 N   E   K   F   K   G   E   A   T   L   T   S   D   K   S   S   N   T   A   Y>

250        260        270        280        290        300
           *          *          *          *          *          *
ATGGAACTCAGCAGCCTGACCTCTGAGGACTCTGCGGTCTATTACTGTGCGGGATTTTTT
TACCTTGAGTCGTCGGACTGGAGACTCCTGAGACGCCAGATAATGACACGCCCTAAAAAA
 M   E   L   S   S   L   T   S   E   D   S   A   V   Y   Y   C   A   G   F   F>

310        320        330        340        350        360
           *          *          *          *          *          *
ACTAGGGCAGTAGGTGGGTCCTACTGGTACCTCGATGTCTGGGGCGCAGGGACCACGGTC
TGATCCCGTCATCCACCCAGGATGACCATGGAGCTACAGACCCCGCGTCCCTGGTGCCAG
 T   R   A   V   G   G   S   Y   W   Y   L   D   V   W   G   A   G   T   T   V>

370        380        390
           *          *          *
ACCGTCTCCTCAGCCAAAACGACACCCCCAAAGCTT
TGGCAGAGGAGTCGGTTTTGCTGTGGGGGTTTCGAA
 T   V   S   S   A   K   T   T   P   P   K   L>
```

Figure 4

```
         10        20        30        40        50        60
          *         *         *         *         *         *
CAAATTGTTCTCACCCAGTCTCCAGCAATCATGTCTGCATCTCCAGGGGAGAAGGTCACC
GTTTAACAAGAGTGGGTCAGAGGTCGTTAGTACAGACGTAGAGGTCCCCTCTTCCAGTGG
 Q  I  V  L  T  Q  S  P  A  I  M  S  A  S  P  G  E  K  V  T>

70        80        90       100       110       120
          *         *         *         *         *         *
ATGACCTGCAGTGCCAGCTCAAGTATAAGTTATATACACTGGTTCCAGCAGAAGCCAGGC
TACTGGACGTCACGGTCGAGTTCATATTCAATATATGTGACCAAGGTCGTCTTCGGTCCG
 M  T  C  S  A  S  S  S  I  S  Y  I  H  W  F  Q  Q  K  P  G>

130       140       150       160       170       180
          *         *         *         *         *         *
ACCTCCCCCAAAAGATGGATTTATGACACATCCAAATTGGTTTCTGGAGTCCCTGCTCGC
TGGAGGGGGTTTTCTACCTAAATACTGTGTAGGTTTAACCAAAGACCTCAGGGACGAGCG
 T  S  P  K  R  W  I  Y  D  T  S  K  L  V  S  G  V  P  A  R>

190       200       210       220       230       240
          *         *         *         *         *         *
TTCAGTGGCAGTGGGTCTGGGACCTCTTATTCTCTCACAATCAGCAACATGGAGGCTGCA
AAGTCACCGTCACCCAGACCCTGGAGAATAAGAGAGTGTTAGTCGTTGTACCTCCGACGT
 F  S  G  S  G  S  G  T  S  Y  S  L  T  I  S  N  M  E  A  A>

250       260       270       280       290       300
          *         *         *         *         *         *
GATGCTGCCACTTATTACTGCCATCAGCGGAGTGCTTCCACGTGGACGTTCGGTGGAGGC
CTACGACGGTGAATAATGACGGTAGTCGCCTCACGAAGGTGCACCTGCAAGCCACCTCCG
 D  A  A  T  Y  Y  C  H  Q  R  S  A  S  T  W  T  F  G  G  G>

310       320       330       340       350
          *         *         *         *         *
ACCAAGTTGGAAATCAAACGGGCTGATGCTGCACCAACTGTATCCGCGGCCGC
TGGTTCAACCTTTAGTTTGCCCGACTACGACGTGGTTGACATAGGCGCCGGCG
 T  K  L  E  I  K  R  A  D  A  A  P  T  V  S  A  A  A>
```

Figure 5

```
           10         20         30         40         50         60
            *          *          *          *          *          *
GAGGTCCAGCTGCAGCAGTCTGGACCGGAGCTGGTAAAGCCTGGGGCTTCAGTGAAGATG
CTCCAGGTCGACGTCGTCAGACCTGGCCTCGACCATTTCGGACCCCGAAGTCACTTCTAC
 E  V  Q  L  Q  Q  S  G  P  E  L  V  K  P  G  A  S  V  K  M>

70         80         90        100        110        120
            *          *          *          *          *          *
TCCTGCAAGGCTTCTGGGTACACTTTCACTACCTATGTTATGCACTGGGTGAAGCAGAAG
AGGACGTTCCGAAGACCCATGTGAAAGTGATGGATACAATACGTGACCCACTTCGTCTTC
 S  C  K  A  S  G  Y  T  F  T  T  Y  V  M  H  W  V  K  Q  K>

130        140        150        160        170        180
            *          *          *          *          *          *
CCTGGGCAGGGCCTTGAGTGGATTGGATATATTAATCCTTACAATGATGGTACTAACTAC
GGACCCGTCCCGGAACTCACCTAACCTATATAATTAGGAATGTTACTACCATGATTGATG
 P  G  Q  G  L  E  W  I  G  Y  I  N  P  Y  N  D  G  T  N  Y>

190        200        210        220        230        240
            *          *          *          *          *          *
AATGAGAAGTTCAAAGGCAAGGCCACACTGACCTCAGACAAATCCTCCAGTACAGCCTAC
TTACTCTTCAAGTTTCCGTTCCGGTGTGACTGGAGTCTGTTTAGGAGGTCATGTCGGATG
 N  E  K  F  K  G  K  A  T  L  T  S  D  K  S  S  S  T  A  Y>

250        260        270        280        290        300
            *          *          *          *          *          *
ATGGAGCTCAGCACCCTGACCTCTGAGGACTCTGCGGTCTATTACTGTGCGGAATTTATT
TACCTCGAGTCGTGGGACTGGAGACTCCTGAGACGCCAGATAATGACACGCCTTAAATAA
 M  E  L  S  T  L  T  S  E  D  S  A  V  Y  Y  C  A  E  F  I>

310        320        330        340        350        360
            *          *          *          *          *          *
ACTAAGACAGTCGGTGGGTCCAACTGGTACCTCGATGTCTGGGGCGCAGGGACCACGGTC
TGATTCTGTCAGCCACCCAGGTTGACCATGGAGCTACAGACCCCGCGTCCCTGGTGCCAG
 T  K  T  V  G  G  S  N  W  Y  L  D  V  W  G  A  G  T  T  V>

370        380        390
            *          *          *
ACCGTCTCCTCAGCCAAAACGACACCCCCAAAGCTT
TGGCAGAGGAGTCGGTTTTGCTGTGGGGGTTTCGAA
 T  V  S  S  A  K  T  T  P  P  K  L>
```

Figure 6

```
          10         20         30         40         50         60
           *          *          *          *          *          *
CAAATTGTTCTCACCCAGTCTCCAGCAATCATGTCTGCTTCTCCAGGGGAGAAGGTCACC
GTTTAACAAGAGTGGGTCAGAGGTCGTTAGTACAGACGAAGAGGTCCCCTCTTCCAGTGG
  Q  I  V  L  T  Q  S  P  A  I  M  S  A  S  P  G  E  K  V  T>

70         80         90        100        110        120
           *          *          *          *          *          *
ATGACCTGCAGTGCCAGCTCAAGTATAAGTTACATACACTGGTTCCAACAGAAGCCAGGC
TACTGGACGTCACGGTCGAGTTCATATTCAATGTATGTGACCAAGGTTGTCTTCGGTCCG
  M  T  C  S  A  S  S  S  I  S  Y  I  H  W  F  Q  Q  K  P  G>

130        140        150        160        170        180
           *          *          *          *          *          *
ACCTCCCCCAAAAGATGGATTTATGACACATCCAAACTGCCTTCTGGAGTCCCTGCTCGC
TGGAGGGGGTTTTCTACCTAAATACTGTGTAGGTTTGACGGAAGACCTCAGGGACGAGCG
  T  S  P  K  R  W  I  Y  D  T  S  K  L  P  S  G  V  P  A  R>

190        200        210        220        230        240
           *          *          *          *          *          *
TTCAGTGGCAGTGGGTCTGGGACCTCTTATTCTCTCACAATCAGCAGCATGGAGGCTGAA
AAGTCACCGTCACCCAGACCCTGGAGAATAAGAGAGTGTTAGTCGTCGTACCTCCGACTT
  F  S  G  S  G  S  G  T  S  Y  S  L  T  I  S  S  M  E  A  E>

250        260        270        280        290        300
           *          *          *          *          *          *
GATGCTGCCACTTATTACTGCCATCAGCGGAGTAGTTACACGTGGACGTTCGGTGGAGGC
CTACGACGGTGAATAATGACGGTAGTCGCCTCATCAATGTGCACCTGCAAGCCACCTCCG
  D  A  A  T  Y  Y  C  H  Q  R  S  S  Y  T  W  T  F  G  G  G>

310        320        330        340        350
           *          *          *          *          *
ACCAAGCTGGAAATCAAACGGGCTGATGCTGCACCAACTGTATCCGCGGCCGC
TGGTTCGACCTTTAGTTTGCCCGACTACGACGTGGTTGACATAGGCGCCGGCG
  T  K  L  E  I  K  R  A  D  A  A  P  T  V  S  A  A  A>
```

Figure 7

SEQUENCE LISTING

<160> NUMBER OF SEQ ID NOS: 42

<210> SEQ ID NO 1
<211> LENGTH: 396
<212> TYPE: DNA
<213> ORGANISM: Mus musculus
<220> FEATURE:
<221> NAME/KEY: CDS
<222> LOCATION: (1)..(396)

<400> SEQUENCE: 1 gag gtg cag ctg caa cag tct gga cct gag ctg gta aag cct ggg gct    48
Glu Val Gln Leu Gln Gln Ser Gly Pro Glu Leu Val Lys Pro Gly Ala
1               5                   10                  15

| | | |
|---|---|---|
| tca gtg aag atg tcc tgc aag gct tct gga tac aca ttc act agc tat<br>Ser Val Lys Met Ser Cys Lys Ala Ser Gly Tyr Thr Phe Thr Ser Tyr<br>     20                      25                      30 | | 96 |
| gtt ata cac tgg gtg aaa cag aag cct ggg cag ggc ctt gag tgg att<br>Val Ile His Trp Val Lys Gln Lys Pro Gly Gln Gly Leu Glu Trp Ile<br>        35                    40                    45 | | 144 |
| gga tat att aat cct tac aac tat gat act aaa tac aat gag aag ttc<br>Gly Tyr Ile Asn Pro Tyr Asn Tyr Asp Thr Lys Tyr Asn Glu Lys Phe<br>50                      55                      60 | | 192 |
| aaa ggc gag gcc aca ctg act tca gac aaa tcc tcc aat aca gcc tac<br>Lys Gly Glu Ala Thr Leu Thr Ser Asp Lys Ser Ser Asn Thr Ala Tyr<br>65                        70                      75                      80 | | 240 |
| atg gaa ctc agc agc ctg acc tct gag gac tct gcg gtc tat tac tgt<br>Met Glu Leu Ser Ser Leu Thr Ser Glu Asp Ser Ala Val Tyr Tyr Cys<br>                    85                      90                      95 | | 288 |
| gcg gga ttt ttt act agg gca gta ggt ggg tcc tac tgg tac ctc gat<br>Ala Gly Phe Phe Thr Arg Ala Val Gly Gly Ser Tyr Trp Tyr Leu Asp<br>               100                      105                   110 | | 336 |
| gtc tgg ggc gca ggg acc acg gtc acc gtc tcc tca gcc aaa acg aca<br>Val Trp Gly Ala Gly Thr Thr Val Thr Val Ser Ser Ala Lys Thr Thr<br>115                        120                      125 | | 384 |
| ccc cca aag ctt<br>Pro Pro Lys Leu<br>    130 | | 396 |

<210> SEQ ID NO 2
<211> LENGTH: 132
<212> TYPE: PRT
<213> ORGANISM: Mus musculus

<400> SEQUENCE: 2

Glu Val Gln Leu Gln Gln Ser Gly Pro Glu Leu Val Lys Pro Gly Ala
1                       5                      10                      15

Ser Val Lys Met Ser Cys Lys Ala Ser Gly Tyr Thr Phe Thr Ser Tyr
               20                      25                      30

Val Ile His Trp Val Lys Gln Lys Pro Gly Gln Gly Leu Glu Trp Ile
          35                      40                    45

Gly Tyr Ile Asn Pro Tyr Asn Tyr Asp Thr Lys Tyr Asn Glu Lys Phe
    50                      55                      60

Lys Gly Glu Ala Thr Leu Thr Ser Asp Lys Ser Ser Asn Thr Ala Tyr
65                      70                      75                      80

Met Glu Leu Ser Ser Leu Thr Ser Glu Asp Ser Ala Val Tyr Tyr Cys
               85                      90                      95

Ala Gly Phe Phe Thr Arg Ala Val Gly Gly Ser Tyr Trp Tyr Leu Asp
               100                      105                   110

Val Trp Gly Ala Gly Thr Thr Val Thr Val Ser Ser Ala Lys Thr Thr
115                        120                      125

Pro Pro Lys Leu
    130

<210> SEQ ID NO 3
<211> LENGTH: 354
<212> TYPE: DNA
<213> ORGANISM: Mus musculus
<220> FEATURE:
<221> NAME/KEY: CDS
<222> LOCATION: (1)..(354)

<400> SEQUENCE: 3

| | |
|---|---|
| caa att gtt ctc acc cag tct cca gca atc atg tct gca tct cca ggg | 48 |

```
Gln Ile Val Leu Thr Gln Ser Pro Ala Ile Met Ser Ala Ser Pro Gly
1               5                   10                  15 gag aag gtc acc atg acc tgc agt gcc agc tca agt ata agt tat ata      96
Glu Lys Val Thr Met Thr Cys Ser Ala Ser Ser Ser Ile Ser Tyr Ile
                20                  25                  30 cac tgg ttc cag cag aag cca ggc acc tcc ccc aaa aga tgg att tat     144
His Trp Phe Gln Gln Lys Pro Gly Thr Ser Pro Lys Arg Trp Ile Tyr
            35                  40                  45 gac aca tcc aaa ttg gtt tct gga gtc cct gct cgc ttc agt ggc agt     192
Asp Thr Ser Lys Leu Val Ser Gly Val Pro Ala Arg Phe Ser Gly Ser
        50                  55                  60 ggg tct ggg acc tct tat tct ctc aca atc agc aac atg gag gct gca     240
Gly Ser Gly Thr Ser Tyr Ser Leu Thr Ile Ser Asn Met Glu Ala Ala
65                  70                  75                  80 gat gct gcc act tat tac tgc cat cag cgg agt gct tcc acg tgg acg     288
Asp Ala Ala Thr Tyr Tyr Cys His Gln Arg Ser Ala Ser Thr Trp Thr
                85                  90                  95 ttc ggt gga ggc acc aag ttg gaa atc aaa cgg gct gat gct gca cca     336
Phe Gly Gly Gly Thr Lys Leu Glu Ile Lys Arg Ala Asp Ala Ala Pro
            100                 105                 110 act gta tcc gcg gcc gcc                                              354
Thr Val Ser Ala Ala Ala
        115

<210> SEQ ID NO 4
<211> LENGTH: 118
<212> TYPE: PRT
<213> ORGANISM: Mus musculus

<400> SEQUENCE: 4

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Ile Ser Tyr Ile
                20                  25                  30

His Trp Phe Gln Gln Lys Pro Gly Thr Ser Pro Lys Arg Trp Ile Tyr
            35                  40                  45

Asp Thr Ser Lys Leu Val Ser Gly Val Pro Ala Arg Phe Ser Gly Ser
        50                  55                  60

Gly Ser Gly Thr Ser Tyr Ser Leu Thr Ile Ser Asn Met Glu Ala Ala
65                  70                  75                  80

Asp Ala Ala Thr Tyr Tyr Cys His Gln Arg Ser Ala Ser Thr Trp Thr
                85                  90                  95

Phe Gly Gly Gly Thr Lys Leu Glu Ile Lys Arg Ala Asp Ala Ala Pro
            100                 105                 110

Thr Val Ser Ala Ala Ala
        115

<210> SEQ ID NO 5
<211> LENGTH: 396
<212> TYPE: DNA
<213> ORGANISM: Mus musculus
<220> FEATURE:
<221> NAME/KEY: CDS
<222> LOCATION: (1)..(396)

<400> SEQUENCE: 5 gag gtc cag ctg cag cag tct gga ccg gag ctg gta aag cct ggg gct      48
Glu Val Gln Leu Gln Gln Ser Gly Pro Glu Leu Val Lys Pro Gly Ala
1               5                   10                  15 tca gtg aag atg tcc tgc aag gct tct ggg tac act ttc act acc tat      96
```

```
Ser Val Lys Met Ser Cys Lys Ala Ser Gly Tyr Thr Phe Thr Thr Tyr
            20                  25                  30 gtt atg cac tgg gtg aag cag aag cct ggg cag ggc ctt gag tgg att       144
Val Met His Trp Val Lys Gln Lys Pro Gly Gln Gly Leu Glu Trp Ile
            35                  40                  45 gga tat att aat cct tac aat gat ggt act aac tac aat gag aag ttc       192
Gly Tyr Ile Asn Pro Tyr Asn Asp Gly Thr Asn Tyr Asn Glu Lys Phe
 50                  55                  60 aaa ggc aag gcc aca ctg acc tca gac aaa tcc tcc agt aca gcc tac       240
Lys Gly Lys Ala Thr Leu Thr Ser Asp Lys Ser Ser Ser Thr Ala Tyr
 65                  70                  75                  80 atg gag ctc agc acc ctg acc tct gag gac tct gcg gtc tat tac tgt       288
Met Glu Leu Ser Thr Leu Thr Ser Glu Asp Ser Ala Val Tyr Tyr Cys
                 85                  90                  95 gcg gaa ttt att act aag aca gtc ggt ggg tcc aac tgg tac ctc gat       336
Ala Glu Phe Ile Thr Lys Thr Val Gly Gly Ser Asn Trp Tyr Leu Asp
                100                 105                 110 gtc tgg ggc gca ggg acc acg gtc acc gtc tcc tca gcc aaa acg aca       384
Val Trp Gly Ala Gly Thr Thr Val Thr Val Ser Ser Ala Lys Thr Thr
            115                 120                 125 ccc cca aag ctt                                                       396
Pro Pro Lys Leu
    130

<210> SEQ ID NO 6
<211> LENGTH: 132
<212> TYPE: PRT
<213> ORGANISM: Mus musculus

<400> SEQUENCE: 6

Glu Val Gln Leu Gln Gln Ser Gly Pro Glu Leu Val Lys Pro Gly Ala
1               5                  10                  15

Ser Val Lys Met Ser Cys Lys Ala Ser Gly Tyr Thr Phe Thr Thr Tyr
            20                  25                  30

Val Met His Trp Val Lys Gln Lys Pro Gly Gln Gly Leu Glu Trp Ile
            35                  40                  45

Gly Tyr Ile Asn Pro Tyr Asn Asp Gly Thr Asn Tyr Asn Glu Lys Phe
 50                  55                  60

Lys Gly Lys Ala Thr Leu Thr Ser Asp Lys Ser Ser Ser Thr Ala Tyr
 65                  70                  75                  80

Met Glu Leu Ser Thr Leu Thr Ser Glu Asp Ser Ala Val Tyr Tyr Cys
                 85                  90                  95

Ala Glu Phe Ile Thr Lys Thr Val Gly Gly Ser Asn Trp Tyr Leu Asp
                100                 105                 110

Val Trp Gly Ala Gly Thr Thr Val Thr Val Ser Ser Ala Lys Thr Thr
            115                 120                 125

Pro Pro Lys Leu
    130

<210> SEQ ID NO 7
<211> LENGTH: 354
<212> TYPE: DNA
<213> ORGANISM: Mus musculus
<220> FEATURE:
<221> NAME/KEY: CDS
<222> LOCATION: (1)..(354)

<400> SEQUENCE: 7 caa att gtt ctc acc cag tct cca gca atc atg tct gct tct cca ggg        48
Gln Ile Val Leu Thr Gln Ser Pro Ala Ile Met Ser Ala Ser Pro Gly
```

```
                1               5                      10                       15
gag aag gtc acc atg acc tgc agt gcc agc tca agt ata agt tac ata           96
Glu Lys Val Thr Met Thr Cys Ser Ala Ser Ser Ser Ile Ser Tyr Ile
             20                  25                      30 cac tgg ttc caa cag aag cca ggc acc tcc ccc aaa aga tgg att tat           144
His Trp Phe Gln Gln Lys Pro Gly Thr Ser Pro Lys Arg Trp Ile Tyr
         35                  40                      45 gac aca tcc aaa ctg cct tct gga gtc cct gct cgc ttc agt ggc agt           192
Asp Thr Ser Lys Leu Pro Ser Gly Val Pro Ala Arg Phe Ser Gly Ser
     50                  55                      60 ggg tct ggg acc tct tat tct ctc aca atc agc agc atg gag gct gaa           240
Gly Ser Gly Thr Ser Tyr Ser Leu Thr Ile Ser Ser Met Glu Ala Glu
 65                  70                      75                      80 gat gct gcc act tat tac tgc cat cag cgg agt agt tac acg tgg acg           288
Asp Ala Ala Thr Tyr Tyr Cys His Gln Arg Ser Ser Tyr Thr Trp Thr
                 85                      90                      95 ttc ggt gga ggc acc aag ctg gaa atc aaa cgg gct gat gct gca cca           336
Phe Gly Gly Gly Thr Lys Leu Glu Ile Lys Arg Ala Asp Ala Ala Pro
             100                     105                     110 act gta tcc gcg gcc gcc                                                   354
Thr Val Ser Ala Ala Ala
        115

<210> SEQ ID NO 8
<211> LENGTH: 118
<212> TYPE: PRT
<213> ORGANISM: Mus musculus

<400> SEQUENCE: 8

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Ile Ser Tyr Ile
            20                  25                  30

His Trp Phe Gln Gln Lys Pro Gly Thr Ser Pro Lys Arg Trp Ile Tyr
        35                  40                  45

Asp Thr Ser Lys Leu Pro Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys His Gln Arg Ser Ser Tyr Thr Trp Thr
                85                  90                  95

Phe Gly Gly Gly Thr Lys Leu Glu Ile Lys Arg Ala Asp Ala Ala Pro
            100                 105                 110

Thr Val Ser Ala Ala Ala
        115

<210> SEQ ID NO 9
<211> LENGTH: 14
<212> TYPE: PRT
<213> ORGANISM: Artificial Sequence
<220> FEATURE:
<223> OTHER INFORMATION: Oligopeptide
<220> FEATURE:
<221> NAME/KEY: MISC_FEATURE
<222> LOCATION: (1)..(14)

<400> SEQUENCE: 9

Asp Leu Pro Asp Ala Ser Val Asn Gly Trp Ser Ser Asp Glu
1               5                   10
```

<210> SEQ ID NO 10
<211> LENGTH: 24
<212> TYPE: PRT
<213> ORGANISM: Artificial Sequence
<220> FEATURE:
<223> OTHER INFORMATION: Oligopeptide
<220> FEATURE:
<221> NAME/KEY: MISC_FEATURE
<222> LOCATION: (1)..(24)
<223> OTHER INFORMATION: TIRC7 peptide 7c

<400> SEQUENCE: 10

Asp Leu Pro Asp Ala Ser Val Asn Gly Trp Ser Ser Asp Glu Glu Lys
 1               5                   10                  15

Ala Gly Gly Leu Asp Asp Glu Glu
            20

<210> SEQ ID NO 11
<211> LENGTH: 24
<212> TYPE: PRT
<213> ORGANISM: Artificial Sequence
<220> FEATURE:
<223> OTHER INFORMATION: Oligopeptide
<220> FEATURE:
<221> NAME/KEY: MISC_FEATURE
<222> LOCATION: (1)..(24)
<223> OTHER INFORMATION: TIRC7 peptide 4

<400> SEQUENCE: 11

Val Glu Phe Gln Asn Lys Phe Tyr Ser Gly Thr Gly Tyr Lys Leu Ser
 1               5                   10                  15

Pro Phe Asp Phe Ala Ala Thr Asp
            20

<210> SEQ ID NO 12
<211> LENGTH: 20
<212> TYPE: DNA
<213> ORGANISM: Artificial Sequence
<220> FEATURE:
<223> OTHER INFORMATION: Oligonucleotide

<400> SEQUENCE: 12
gcgcgcaagc ttgccgccac                                        20

<210> SEQ ID NO 13
<211> LENGTH: 35
<212> TYPE: DNA
<213> ORGANISM: Artificial Sequence
<220> FEATURE:
<223> OTHER INFORMATION: Oligonucleotide

<400> SEQUENCE: 13
gaataggcca tggcgcaggt gcagctgaag gagtc                       35

<210> SEQ ID NO 14
<211> LENGTH: 35
<212> TYPE: DNA
<213> ORGANISM: Artificial Sequence
<220> FEATURE:
<223> OTHER INFORMATION: Oligonucleotide

<400> SEQUENCE: 14
gaataggcca tggcgcaggt gcagctgaag cagtc                       35

<210> SEQ ID NO 15
<211> LENGTH: 35
<212> TYPE: DNA

```
<213> ORGANISM: Artificial Sequence
<220> FEATURE:
<223> OTHER INFORMATION: Oligonucleotide

<400> SEQUENCE: 15
gaataggcca tggcgcaggt tactctgaaa gagtc                                35

<210> SEQ ID NO 16
<211> LENGTH: 36
<212> TYPE: DNA
<213> ORGANISM: Artificial Sequence
<220> FEATURE:
<223> OTHER INFORMATION: Oligonucleotide

<400> SEQUENCE: 16
gaataggcca tggcggaggt ccagctgcaa caatct                               36

<210> SEQ ID NO 17
<211> LENGTH: 35
<212> TYPE: DNA
<213> ORGANISM: Artificial Sequence
<220> FEATURE:
<223> OTHER INFORMATION: Oligonucleotide

<400> SEQUENCE: 17
gaataggcca tggcggaggt ccagctgcag cagtc                                35

<210> SEQ ID NO 18
<211> LENGTH: 36
<212> TYPE: DNA
<213> ORGANISM: Artificial Sequence
<220> FEATURE:
<223> OTHER INFORMATION: Oligonucleotide

<400> SEQUENCE: 18
gaataggcca tggcgcaggt ccaactgcag cagcct                               36

<210> SEQ ID NO 19
<211> LENGTH: 35
<212> TYPE: DNA
<213> ORGANISM: Artificial Sequence
<220> FEATURE:
<223> OTHER INFORMATION: Oligonucleotide

<400> SEQUENCE: 19
gaataggcca tggcggaggt gaacctggtg gagtc                                35

<210> SEQ ID NO 20
<211> LENGTH: 35
<212> TYPE: DNA
<213> ORGANISM: Artificial Sequence
<220> FEATURE:
<223> OTHER INFORMATION: Oligonucleotide

<400> SEQUENCE: 20
gaataggcca tggcggaggt gaagctggtg gaatc                                35

<210> SEQ ID NO 21
<211> LENGTH: 35
<212> TYPE: DNA
<213> ORGANISM: Artificial Sequence
<220> FEATURE:
<223> OTHER INFORMATION: Oligonucleotide

<400> SEQUENCE: 21
gaataggcca tggcggatgt gaacttggaa gtgtc                                35
```

<210> SEQ ID NO 22
<211> LENGTH: 35
<212> TYPE: DNA
<213> ORGANISM: Artificial Sequence
<220> FEATURE:
<223> OTHER INFORMATION: Oligonucleotide

<400> SEQUENCE: 22
gaataggcca tggcggaggt ccagctgcaa cagtc                          35

<210> SEQ ID NO 23
<211> LENGTH: 35
<212> TYPE: DNA
<213> ORGANISM: Artificial Sequence
<220> FEATURE:
<223> OTHER INFORMATION: Oligonucleotide

<400> SEQUENCE: 23
gaataggcca tggcggaggt gcagctggag gagtc                          35

<210> SEQ ID NO 24
<211> LENGTH: 36
<212> TYPE: DNA
<213> ORGANISM: Artificial Sequence
<220> FEATURE:
<223> OTHER INFORMATION: Oligonucleotide

<400> SEQUENCE: 24
ggccagtgga taaacctttg ggggtgtcgt tttggc                         36

<210> SEQ ID NO 25
<211> LENGTH: 38
<212> TYPE: DNA
<213> ORGANISM: Artificial Sequence
<220> FEATURE:
<223> OTHER INFORMATION: Oligonucleotide

<400> SEQUENCE: 25
tacaggatcc acgcgtagat gttttgatga cccaaact                       38

<210> SEQ ID NO 26
<211> LENGTH: 38
<212> TYPE: DNA
<213> ORGANISM: Artificial Sequence
<220> FEATURE:
<223> OTHER INFORMATION: Oligonucleotide

<400> SEQUENCE: 26
tacaggatcc acgcgtagat attgtgatga cgcaggct                       38

<210> SEQ ID NO 27
<211> LENGTH: 35
<212> TYPE: DNA
<213> ORGANISM: Artificial Sequence
<220> FEATURE:
<223> OTHER INFORMATION: Oligonucleotide

<400> SEQUENCE: 27
tacaggatcc acgcgtagat attgtgataa cccag                          35

<210> SEQ ID NO 28
<211> LENGTH: 38
<212> TYPE: DNA
<213> ORGANISM: Artificial Sequence
<220> FEATURE:

<223> OTHER INFORMATION: Oligonucleotide

<400> SEQUENCE: 28
tacaggatcc acgcgtagac attgtgctga cccaatct                    38

<210> SEQ ID NO 29
<211> LENGTH: 38
<212> TYPE: DNA
<213> ORGANISM: Artificial Sequence
<220> FEATURE:
<223> OTHER INFORMATION: Oligonucleotide

<400> SEQUENCE: 29
tacaggatcc acgcgtagac attgtgatga cccagtct                    38

<210> SEQ ID NO 30
<211> LENGTH: 38
<212> TYPE: DNA
<213> ORGANISM: Artificial Sequence
<220> FEATURE:
<223> OTHER INFORMATION: Oligonucleotide

<400> SEQUENCE: 30
tacaggatcc acgcgtagat attgtgctaa ctcagtct                    38

<210> SEQ ID NO 31
<211> LENGTH: 38
<212> TYPE: DNA
<213> ORGANISM: Artificial Sequence
<220> FEATURE:
<223> OTHER INFORMATION: Oligonucleotide

<400> SEQUENCE: 31
tacaggatcc acgcgtagat atccagatga cacagact                    38

<210> SEQ ID NO 32
<211> LENGTH: 38
<212> TYPE: DNA
<213> ORGANISM: Artificial Sequence
<220> FEATURE:
<223> OTHER INFORMATION: Oligonucleotide

<400> SEQUENCE: 32
tacaggatcc acgcgtagac atccagctga ctcagtct                    38

<210> SEQ ID NO 33
<211> LENGTH: 38
<212> TYPE: DNA
<213> ORGANISM: Artificial Sequence
<220> FEATURE:
<223> OTHER INFORMATION: Oligonucleotide

<400> SEQUENCE: 33
tacaggatcc acgcgtacaa attgttctca cccagtct                    38

<210> SEQ ID NO 34
<211> LENGTH: 38
<212> TYPE: DNA
<213> ORGANISM: Artificial Sequence
<220> FEATURE:
<223> OTHER INFORMATION: Oligonucleotide

<400> SEQUENCE: 34
tacaggatcc acgcgtagac attctgatga cccagtct                    38

```
<210> SEQ ID NO 35
<211> LENGTH: 39
<212> TYPE: DNA
<213> ORGANISM: Artificial Sequence
<220> FEATURE:
<223> OTHER INFORMATION: Oligonucleotide

<400> SEQUENCE: 35
tgacaagctt gcggccgcgg atacagttgg tgcagcatc                              39

<210> SEQ ID NO 36
<211> LENGTH: 98
<212> TYPE: DNA
<213> ORGANISM: Artificial Sequence
<220> FEATURE:
<223> OTHER INFORMATION: Polynucleotide

<400> SEQUENCE: 36
gcgcgcaagc ttgccgccac catgggatgg agctgtatca tcctcttctt ggtagcaaca      60
gctacaggtg tccactccga ggtgcagctg caacagtc                              98

<210> SEQ ID NO 37
<211> LENGTH: 45
<212> TYPE: DNA
<213> ORGANISM: Artificial Sequence
<220> FEATURE:
<223> OTHER INFORMATION: Oligonucleotide

<400> SEQUENCE: 37
tttatatggg cccttggtgg aggctgagga cacggtgacc gtggt                      45

<210> SEQ ID NO 38
<211> LENGTH: 99
<212> TYPE: DNA
<213> ORGANISM: Artificial Sequence
<220> FEATURE:
<223> OTHER INFORMATION: Polynucleotide

<400> SEQUENCE: 38
gcgcgcaagc ttgccgccac catgggatgg agctgtatca tcctcttctt ggtagcaaca      60
gctacaggtg tccactccca aattgttctc acccagtct                             99

<210> SEQ ID NO 39
<211> LENGTH: 33
<212> TYPE: DNA
<213> ORGANISM: Artificial Sequence
<220> FEATURE:
<223> OTHER INFORMATION: Oligonucleotide

<400> SEQUENCE: 39
atatggcgta cgtttgattt ccaacttggt gcc                                   33

<210> SEQ ID NO 40
<211> LENGTH: 35
<212> TYPE: DNA
<213> ORGANISM: Artificial Sequence
<220> FEATURE:
<223> OTHER INFORMATION: Oligonucleotide

<400> SEQUENCE: 40
gaataggcca tggcggatgt gaagctgcag gagtc                                 35

<210> SEQ ID NO 41
<211> LENGTH: 26
<212> TYPE: DNA
```

```
<213> ORGANISM: Artificial Sequence
<220> FEATURE:
<223> OTHER INFORMATION: Oligonucleotide

<400> SEQUENCE: 41 cacaatttc ttgtccacct tgggtgc                                              26

<210> SEQ ID NO 42
<211> LENGTH: 27
<212> TYPE: DNA
<213> ORGANISM: Artificial Sequence
<220> FEATURE:
<223> OTHER INFORMATION: Oligonucleotide

<400> SEQUENCE: 42
ctcattcctg ttgaagctct tgacaat                                             27
```

THERAPEUTIC ANTI-TIRC7 ANTIBODIES FOR USE IN IMMUNE RELATED AND OTHER DISEASES

CROSS-REFERENCE TO RELATED APPLICATIONS

This application is a continuation of U.S. Ser. No. 13/458,981, filed Apr. 27, 2012; which is a continuation of U.S. Ser. No. 13/233,867, filed Sep. 15, 2011, which is a continuation of U.S. Ser. No. 10/513,539, filed Dec. 19, 2005; which is a §371 national stage of PCT International Application No. PCT/EP02/14734, filed Dec. 23, 2002, claiming priority of European Application No. 01 130 730.3, filed Dec. 21, 2001, the contents of which are hereby incorporated by reference.

This application incorporates by reference nucleotide and/or amino acid sequences which are present in the file named "121221_5120_73284-AAA_Substitute_Sequence_Listing_CSS.txt" which is 20 kilobytes in size, and which was created Dec. 21, 2012 in the IBM-PC machine format, having an operating system compatibility with MS-Windows, which is contained in the text file Dec. 21, 2012 as part of this application.

BACKGROUND

The present invention relates to anti-T-cell immune response cDNA 7 (TIRC7) antibodies and uses thereof. In particular, the anti-TIRC7 antibodies of the invention are capable of suppressing the proliferation of activated cells of the immune system. Furthermore, the present invention relates to compositions comprising said antibodies and to methods of modulating immune cell proliferation, and treating immune response related diseases.

Several documents are cited throughout the text of this specification. Each of the documents cited herein (including any manufacturer's specifications, instructions, etc.) are hereby incorporated herein by reference; however, there is no admission that any document cited is indeed prior art as to the present invention.

T-cell activation is a serial process involving multiple signaling pathways and sequential changes in gene expression resulting in differentiation of T-cells into distinct subpopulations, i.e. Th1 and Th2, which are distinguishable by their pattern of cytokine production and characterize the mode of cellular immune response. The T-cell response is initiated by the interaction of the antigen-specific T-cell receptor (TCR) with peptide presented by major histocompatibility complex (MHC) molecules on the surface of antigen presenting cells (APCs). Additional signals are provided by a network of receptor-ligand interactions mediated by a number of membrane proteins such as CD28/CTLA4 and B7, CD40/CD40L, LFA-1 and ICAM-1 (Lenschow, Science 257 (1992), 789-792; Linsley, Annu. Rev. Immunol. 11 (1993), 191-212; Xu, Immunity 1 (1994), 423-431; Bachmann, Immunity 7 (1997), 549-557; Schwartz, *Cell* 71 (1992), 1065-1068) collectively called costimulatory signals (Perez, Immunity 6 (1997), 411). These membrane proteins can alter T-cell activation in distinct ways (Bachmann, Immunity 7 (1997), 549-557) and regulate the immune response by the integration of positive and negative signals provided by these molecules (Bluestone, Immunity 2 (1995), 555-559; Perez, Immunity 6 (1997), 411). Many of the agents which are effective in modulating the cellular immune response either interfere with the T-cell receptor (Cosimi, Transplantation 32 (1981), 535-539) block costimulatory signaling (Larsen, Nature 381 (1996), 434-438; Blazar J. Immuno. 157 (1996), 3250-3259; Kirk, Proc. Natl. Acad. Sci. USA 94 (1997), 8789-8794; Linsley, Science 257 (1992), 792-95; Turka, Proc. Natl. Acad. Sci. USA 89 (1992), 11102-11105) or inhibit intracellular activation signals downstream from these primary cell membrane triggers (Schreiber and Crabtree, Immunology Today 13 (1992), 136-42). Therapeutic prevention of T-cell activation in organ transplantation and autoimmune diseases presently relies on panimmunosupressive drugs interfering with downstream intracellular events. Specific modulation of the immune response remains a longstanding goal in immunological research.

In view of the need of therapeutic means for the treatment of diseases related to immune responses of the human body, the technical problem of the present invention is to provide means and methods for modulation of the immune response in a subject. The solution to said technical problem is achieved by providing the embodiments characterized in the claims, and described further below.

SUMMARY

Accordingly, the present invention generally relates to a monoclonal antibody or antigen binding molecule which is capable of binding to an antigen comprising or consisting of the amino acid sequence of any one of SEQ ID NOs: 9 to 11. Those antibodies are preferably capable of inhibiting proliferation of peripheral blood mononuclear cells (PBMCs). In a particularly preferred embodiment said antibody comprises in its variable region at least one complementarity determining region (CDR) of the $V_H$ and/or $V_L$ of the variable region comprising (a) the amino acid sequence depicted in FIG. 4 ($V_H$) (SEQ ID NO: 2) and FIG. 5 ($V_L$) (SEQ ID NO: 4); or (b) the amino acid sequence depicted in FIG. 6 ($V_H$) (SEQ ID NO: 6) and FIG. 7 ($V_L$) (SEQ ID NO: 8).

The person skilled in the art knows that each variable domain (the heavy chain $V_H$ and light chain $V_L$) of an antibody comprises three hypervariable regions, sometimes called complementarity determining regions or "CDRs" flanked by four relatively conserved framework regions or "FRs". The CDRs contained in the variable regions of the antibody of the invention can be determined, e.g., according to Kabat, Sequences of Proteins of Immunological Interest (U.S. Department of Health and Human Services, third edition, 1983, fourth edition, 1987, fifth edition 1990). The person skilled in the art will readily appreciate that the variable domain of the antibody having the above-described variable domain can be used for the construction of other polypeptides or antibodies of desired specificity and biological function. Thus, the present invention also encompasses polypeptides and antibodies comprising at least one CDR of the above-described variable domain and which advantageously have substantially the same or similar binding properties as the antibody described in the appended examples. The person skilled in the art will readily appreciate that using the variable domains or CDRs described herein antibodies can be constructed according to methods known in the art, e.g., as described in EP-A1 0 451 216 and EP-A1 0 549 581. Furthermore, the person skilled in the art knows that binding affinity may be enhanced by making amino acid substitutions within the CDRs or within the hypervariable loops (Chothia and Lesk, J. Mol. Biol. 196 (1987), 901-917) which partially overlap with the CDRs as defined by Kabat. Thus, the present invention also relates to antibodies wherein one or more of the mentioned CDRs comprise one or more, preferably not more than two amino acid substitutions. Preferably, the antibody of the invention comprises in one or both of its immunoglobulin chains two or all three CDRs of the above mentioned variable regions shown in FIGS. 4-5 and FIGS. 6-7, respectively.

DETAILED DESCRIPTION

As described in the examples, the antibody of the invention recognizes a fragment of the amino acid sequence from T cell immune response cDNA 7 (TIRC7) protein. The term "TIRC7" as used in accordance with the present invention, denotes a protein which initially has been described to be involved in the signal transduction of T-cell activation and proliferation and that, preferably in a soluble form is capable of inhibiting or suppressing T-cell proliferation in response to alloactivation in a mixed lymphocyte culture or in response to mitogens when exogeneously added to the culture. In vitro translated TIRC7 protein has been shown to be able to efficiently suppress in a dose dependent manner the proliferation of T-cells in response to alloactivation in a mixed lymphocyte culture or in response to mitogens. TIRC7 is known to the person skilled in the art and described, inter alia, in WO99/11782, Utku, Immunity 9 (1998), 509-518 and Heinemann, Genomics 57 (1999), 398-406, which also disclose the amino and nucleic acid sequences of TIRC7.

As it was shown by Utku et al. (Immunity, 1998), polyclonal antibodies against TIRC7 suppressed the proliferation of activated T-cells in MLR in a dose dependent manner. While these promising results suggested the therapeutic use of such antibodies, there was a need for antibodies that have high binding specificity and affinity, and that efficiently suppress, for example, T cell proliferation thereby allowing the use of such antibodies at low doses in order to circumvent possible HAMA responses in a subject. Furthermore, such antibodies may have different or differently pronounced effects on, e.g., cytokine production which can be important in the treatment of certain immune response related diseases, for example graft rejection.

In order to find antibodies which supply the needs mentioned above, mice were immunized with peptides from several domains of TIRC7, which were thought to represent putatively appropriate antigens; see FIG. 1 of WO99/11782. However, while most of these peptides proved to be good antigens for raising polyclonal antibodies, several attempts failed to produce stable hybridomas which secreted antibodies with the desired binding affinity and/or biological activity. However, with three (see Table 1 and SEQ ID NOs: 9 to 11, infra) of six peptides derived from the sequence of several hypothetically extracellular domains of TIRC7, the inventors eventually succeeded with generating stable hybridomas producing the desired monoclonal antibodies. Thus, 192 stable antibody producing hybridomas were received and 42 antibodies were tested; see FIG. 1. From those antibodies 15 antibodies were selected which inhibited cell proliferation (FIG. 2, proliferation assay) as well as the secretion of IFNγ and IL-2 (FIG. 2) of PHA-stimulated human PBMC of healthy donors below 30% calculated in relation to the positive control (100%). Finally three antibodies were selected, #9 and #17, both descended from fusions performed with spleen cells of mice that had been immunized with peptides derived from the largest extracellular loop of TIRC7, and #18, in this case the peptide used for immunization was derived from the extracellular C-Terminus of TIRC7 (FIG. 3); see also Table 1. In accordance with the present invention, it could then surprisingly be shown that chimeric recombinant antibodies comprising the $V_H$- and $V_L$-variable regions of the murine monoclonal antibodies and either the human gamma or kappa constant region exhibit substantially the same specificity, binding affinity and biological activity as the murine donor antibodies.

Accordingly, the antibodies of the present invention are expected to be useful in the modulation of immune responses. Modulating the immune response, as for example by activating or inhibiting the proliferation and/or differentiation of T-cells, B-cells, NK cells, LAK cells, dendritic cells, monocytes, macrophages or other immune system cells, may be useful in treating autoimmune diseases, allergic diseases, and in transplantation therapies where graft vs. host or host vs. graft effects may be undesirable. The antibodies could also be immune stimulants in settings such as cancer, infectious disease, sepsis, wound healing, or immunization. Alternatively, they could be immune suppressants. They could also be used to detect inflammation, and preferably modulate inflammation by activating or inhibiting activation of immune or inflammatory cells. A preferred method involves detecting (and preferably modulating) inflammation in tissues such as inflamed vasculature or leukocytes. Furthermore, the antibodies of the present invention can be used to induce or maintain immune unresponsiveness.

The term "immune unresponsiveness" comprises non-unresponsiveness of immune cell subsets like T-cell or B-cells, NK-cells, monocytes and/or macrophages.

The terms "treatment", "treating" and the like are used herein to generally mean obtaining a desired pharmacological and/or physiological effect. The effect may be prophylactic in terms of completely or partially preventing a disease or symptom thereof and/or may be therapeutic in terms of partially or completely curing a disease and/or adverse effect attributed to the disease. The term "treatment" as used herein covers any treatment of a disease in a mammal, particularly a human, and includes: (a) preventing the disease from occurring in a subject which may be predisposed to the disease but has not yet been diagnosed as having it; (b) inhibiting the disease, i.e. arresting its development; or (c) relieving the disease, i.e. causing regression of the disease.

Furthermore, the term "subject" as employed herein relates to animals in need of amelioration, treatment and/or prevention of immunological diseases as disclosed herein. Most preferably said subject is a human.

Hence, the antibodies described herein can be used for any application described for anti-TIRC7 antibodies before, in particular if therapeutic and in vivo diagnostic uses are envisaged; see for example WO99/11782 and co-pending PCT application no. PCT/EP02/13384, the disclosure content of which is hereby incorporated by reference.

Without intending to be bound by theory, it is believed that the described anti-TIRC7 antibodies are capable of modulating the function (e.g., signaling or adhesive activities) of TIRC7, its family members and/or their ligands, for example by interfering with the interaction of TIRC7 with its ligand. However, irrespective the theory behind the molecular mechanism of action, the antibody of the invention can be characterized by (1) having binding affinity to TIRC7 in the order of at least $10^{-7}$M, preferably at least $10^{-8}$M, more preferably at least $0.5 \times 10^{-8}$M, still more preferably at least $10^{-8}$M, and most preferably at least $10^{-9}$M or $10^{-10}$M and (2) being capable of inhibiting proliferation of mitogen-stimulated PBMCs in an assay as described in Example 1. Preferably, the antibody of the invention and any binding fragment derived thereof is capable of inhibiting the proliferation as well as the secretion of IFNg and IL-2 of PHA-stimulated human PBMC of healthy donors below 30% calculated in relation to the positive control (100%). Most preferably, the antibody or binding fragment is capable of inhibiting the proliferation of PHA-stimulated human PBMC of healthy donors below 25% or even below 20% or more calculated in relation to the positive control (100%).

Thus the present antibodies are preferably capable of modulating, preferably inhibiting proliferation of peripheral blood mononuclear cells (PBMCs). Preferably, the antibodies of the present invention modulate at least one of the following (which are functions of TIRC7 proteins and/or ligands thereof): activation of neutrophils; activation or inhibition of T-cells, B-cells, NK cells, LAK cells, dendritic cells, or other immune system cells; proliferation and/or differentiation of T-cells, B-cells, NK cells, LAK cells, dendritic cells, or other immune system cells; proliferation and/or differentiation of epithelial cells such as breast or intestinal/colonic epithelium cells or keratinocytes. In addition these antibodies preferably are capable of altering homotypic and/or heterotypic adhesion among TIRC7 proteins (i.e., TIRC7 family members) or adhesion of TIRC7 proteins to other TIRC7 ligands.

The antibody of the invention can be a monoclonal antibody, a single chain antibody, chimeric antibody, humanized antibody, xenogeneic antibody, or a fragment and/or a chemically modified derivative of any one thereof that specifically binds TIRC7 antigen also including bispecific antibody, synthetic antibody, antibody fragment, such as Fab, Fv or scFv fragments etc., or a chemically modified derivative of any of these. Antibodies or fragments thereof can be obtained by using methods which are described, e.g., in Harlow and Lane "Antibodies, A Laboratory Manual", CSH Press, Cold Spring Harbor, 1988. When derivatives of said antibodies are obtained by the phage display technique, surface plasmon resonance as employed in the BIAcore system can be used to increase the efficiency of phage antibodies which bind to the same epitope as that of any one of the antibodies described herein (Schier, Human Antibodies Hybridomas 7 (1996), 97-105; Malmborg, J. Immunol. Methods 183 (1995), 7-13). The production of chimeric antibodies is described, for example, in WO89/09622. Methods for the production of humanized antibodies are described in, e.g., EP-A1 0 239 400 and WO90/07861. A further source of antibodies to be utilized in accordance with the present invention are so-called xenogeneic antibodies. The general principle for the production of xenogeneic antibodies such as human antibodies in mice is described in, e.g., WO 91/10741, WO 94/02602, WO 96/34096 and WO 96/33735. As discussed above, the antibody of the invention may exist in a variety of forms besides complete antibodies; including, for example, Fv, Fab and F(ab)$_2$, as well as in single chains; see e.g. WO88/09344. In case of bispecific antibodies where one specificity is directed to TIRC7 and the other preferably to a T cell antigen such as CD3, it is advantageous if the binding site recognizing TIRC7 has a high affinity in order to capture the antigen target cells. On the other hand, the binding affinity of the binding site recognizing, e.g., a T cell stimulatory molecule should be in the order of those of the natural T cell receptor/ligand interaction or of that usually found for the interaction of the T-cell costimulatory molecules with their receptor.

The antibodies of the present invention or their corresponding immunoglobulin chain(s) can be further modified using conventional techniques known in the art, for example, by using amino acid deletion(s), insertion(s), substitution(s), addition(s), and/or recombination(s) and/or any other modification(s) known in the art either alone or in combination. Methods for introducing such modifications in the DNA sequence underlying the amino acid sequence of an immunoglobulin chain are well known to the person skilled in the art; see, e.g., Sambrook, Molecular Cloning A Laboratory Manual, Cold Spring Harbor Laboratory (1989) N.Y. Modifications of the antibody of the invention include chemical and/or enzymatic derivatizations at one or more constituent amino acid, including side chain modifications, backbone modifications, and N- and C-terminal modifications including acetylation, hydroxylation, methylation, amidation, and the attachment of carbohydrate or lipid moieties, cofactors, and the like. Likewise, the present invention encompasses chimeric proteins which comprise the described anti-TIRC7 antibody or some fragment thereof at the amino terminus fused to heterologous molecule such as an immunostimulatory ligand at the carboxyl terminus; see, e.g., WO00/30680 for corresponding technical details.

Hence, the present invention relates to any antibody and similar binding molecules which recognize the same epitope and with substantially the same affinity, or at least 1/10 of the affinity as the antibodies of the invention exemplified herein. Such antibodies and binding molecules can be tested for their binding specificity and affinity by for example using peptide 6 and/or competitive assays with an antibody described in the examples.

In a preferred embodiment, the antibody of the invention is a chimeric or a humanized antibody. Chimeric antibodies are antibodies whose light and heavy chain genes have been constructed, typically by genetic engineering, from immunoglobulin gene segments belonging to different species. For example, the variable (V) segments of the genes from the mouse TIRC7 monoclonal antibody may be joined to human constant (C) segments, such as γ1 and γ3. A typical therapeutic chimeric antibody is thus a hybrid protein consisting of the V or antigen-binding domain from a mouse antibody and the C or effector domain from a human antibody, although other mammalian species may be used as well if for example veterinary application is envisaged. Human constant region DNA sequences can be isolated in accordance with well known procedures from a variety of human cells, but preferably immortalized B-cells (see, Kabat op. cit. and WO87/02671). For example, the human kappa immunoglobulin constant and J region genes and sequences are described in Heiter, Cell 22 (1980), 197-207 and the nucleotide sequence of a human immunoglobulin C gene is described in Ellison, Nucl. Acids Res. 10 (1982), 4071, both of which are incorporated herein by reference. In a particularly preferred embodiment, the antibody of the invention comprises the amino acid sequence of the $V_H$ and/or $V_L$ region as depicted in FIGS. 4 and 5, and 6 and 7, respectively.

In a further embodiment, the present invention relates to an antigen or an epitope thereof which is recognized by an antibody of the invention. Said antigen or epitope may be glycosylated, unglycosylated or partially deglycosylated. As discussed herein and explained in the examples, the present invention features antigens which are particularly suited for eliciting an immune response. For the identification and isolation of antigen and epitopes of the invention conventional epitope mapping can be used; see, e.g., Harlow and Lane, supra. Furthermore, e.g., cDNA libraries can be screened by injecting various cDNAs into oocytes, allowing sufficient time for expression of the cDNA gene products to occur, and testing for the presence of the desired cDNA expression product, for example, by using the antibody of the invention. Alternatively, a cDNA expression library in *E. coli* can be screened indirectly for peptides having at least one epitope of the invention using antibodies of the invention (Chang and Gottlieb, J. Neurosci., 8:2123, 1988). After having revealed the structure of such antigens the rational design of binding partners and/or domains may be possible. For example, folding simulations and computer redesign of structural motifs can be performed using appropriate computer programs (Olszewski, Proteins 25 (1996), 286-299; Hoffman, Comput. Appl. Biosci. 11 (1995), 675-679). Furthermore, computers can be used for the conformational and energetic analysis of detailed protein models (Monge, J. Mol. Biol. 247 (1995), 995-1012; Renouf, Adv. Exp. Med. Biol. 376 (1995), 37-45).

Preferably, the antigen of the invention does not comprise more that 50, preferably not more than 40, and still more preferably not more 30 consecutive amino acids from TIRC7 protein. Preferably, the antigens of the present invention have about 12 to 30 amino acids derived from TIRC7. In a most preferred embodiment, said antigen comprises or consists of the amino acid sequence of peptide 6 (DLPDASVNG-WSSDE, SEQ ID NO: 9), peptide 7c (DLPDASVNGWSS-DEEKAGGLDDEE, SEQ ID NO: 10) and/or peptide 4 (VEFQNKFYSGTGYKLSPFDFAATD, SEQ ID NO: 11). This includes peptides that have been modified or derivatized, such as by glycosylation, acetylation, phosphorylation, and the like.

In another embodiment the present invention relates to a polynucleotide encoding at least a variable region of an immunoglobulin chain of any of the before described antibodies of the invention. One form of immunoglobulin constitutes the basic structural unit of an antibody. This form is a tetramer and consists of two identical pairs of immunoglobulin chains, each pair having one light and one heavy chain. In each pair, the light and heavy chain variable regions or domains are together responsible for binding to an antigen, and the constant regions are responsible for the antibody effector functions. In addition to antibodies, immunoglobulins may exist in a variety of other forms (including less than full-length that retain the desired activities), including, for example, Fv, Fab, and F(ab')$_2$, as well as single chain antibodies (e.g., Huston, Proc. Nat. Acad. Sci. USA 85 (1988), 5879-5883 and Bird, Science 242 (1988), 423-426); see also supra. An immunoglobulin light or heavy chain variable domain consists of a "framework" region interrupted by three hypervariable regions, also called CDRs; see supra. The antibodies of the present invention can be produced by expressing recombinant DNA segments encoding the heavy and light immunoglobulin chain(s) of the antibody invention either alone or in combination.

The polynucleotide of the invention encoding the above described antibody may be, e.g., DNA, cDNA, RNA or synthetically produced DNA or RNA or a recombinantly produced chimeric nucleic acid molecule comprising any of those polynucleotides either alone or in combination. Preferably said polynucleotide is part of a vector. Such vectors may comprise further genes such as marker genes which allow for the selection of said vector in a suitable host cell and under suitable conditions. Preferably, the polynucleotide of the invention is operatively linked to expression control sequences allowing expression in prokaryotic or eukaryotic cells. Expression of said polynucleotide comprises transcription of the polynucleotide into a translatable mRNA. Regulatory elements ensuring expression in eukaryotic cells, preferably mammalian cells, are well known to those skilled in the art. They usually comprise regulatory sequences ensuring initiation of transcription and optionally poly-A signals ensuring termination of transcription and stabilization of the transcript. Additional regulatory elements may include transcriptional as well as translational enhancers, and/or naturally-associated or heterologous promoter regions. In this respect, the person skilled in the art will readily appreciate that the polynucleotides encoding at least the variable domain of the light and/or heavy chain may encode the variable domains of both immunoglobulin chains or only one. Likewise, said polynucleotides may be under the control of the same promoter or may be separately controlled for expression. Possible regulatory elements permitting expression in prokaryotic host cells comprise, e.g., the $P_L$, lac, trp or tac promoter in E. coli, and examples for regulatory elements permitting expression in eukaryotic host cells are the AOX1 or GAL1 promoter in yeast or the CMV-, SV40-, RSV-promoter (Rous sarcoma virus), CMV-enhancer, SV40-enhancer or a globin intron in mammalian and other animal cells. Beside elements which are responsible for the initiation of transcription such regulatory elements may also comprise transcription termination signals, such as the SV40-poly-A site or the tk-poly-A site, downstream of the polynucleotide. Furthermore, depending on the expression system used leader sequences capable of directing the polypeptide to a cellular compartment or secreting it into the medium may be added to the coding sequence of the polynucleotide of the invention and are well known in the art. The leader sequence(s) is (are) assembled in appropriate phase with translation, initiation and termination sequences, and preferably, a leader sequence capable of directing secretion of translated protein, or a portion thereof, into the periplasmic space or extracellular medium. Optionally, the heterologous sequence can encode a fusion protein including C- or N-terminal identification peptide imparting desired characteristics, e.g., stabilization or simplified purification of expressed recombinant product. In this context, suitable expression vectors are known in the art such as Okayama-Berg cDNA expression vector pcDV1 (Pharmacia), pCDM8, pRc/CMV, pcDNA1, pcDNA3 (Invitrogene), or pSPORT1 (GIBCO BRL).

Preferably, the expression control sequences will be eukaryotic promoter systems in vectors capable of transforming or transfecting eukaryotic host cells, but control sequences for prokaryotic hosts may also be used. Once the vector has been incorporated into the appropriate host, the host is maintained under conditions suitable for high level expression of the nucleotide sequences, and, as desired, the collection and purification of the immunoglobulin light chains, heavy chains, light/heavy chain dimers or intact antibodies, binding fragments or other immunoglobulin forms may follow; see, Beychok, Cells of Immunoglobulin Synthesis, Academic Press, N.Y., (1979); see also, e.g., the appended examples.

As described above, the polynucleotide of the invention can be used alone or as part of a vector to express the (poly) peptide of the invention in cells, for, e.g., gene therapy or diagnostics of diseases related to immune diseases. The polynucleotides or vectors of the invention are introduced into the cells which in turn produce the antibody. Gene therapy, which is based on introducing therapeutic genes into cells by ex-vivo or in-vivo techniques is one of the most important applications of gene transfer. Suitable vectors and methods for in-vitro or in-vivo gene therapy are described in the literature and are known to the person skilled in the art; see, e.g., Giordano, Nature Medicine 2 (1996), 534-539; Schaper, Circ. Res. 79 (1996), 911-919; Anderson, Science 256 (1992), 808-813; Isner, Lancet 348 (1996), 370-374; Muhlhauser, Circ. Res. 77 (1995), 1077-1086; Wang, Nature Medicine 2 (1996), 714-716; WO94/29469; WO 97/00957 or Schaper, Current Opinion in Biotechnology 7 (1996), 635-640, and references cited therein. The polynucleotides and vectors of the invention may be designed for direct introduction or for introduction via liposomes, or viral vectors (e.g. adenoviral, retroviral) into the cell. Preferably, said cell is a germ line cell, embryonic cell, or egg cell or derived therefrom, most preferably said cell is a stem cell.

Furthermore, the present invention relates to vectors, particularly plasmids, cosmids, viruses and bacteriophages used conventionally in genetic engineering that comprise a polynucleotide encoding a variable domain of an immunoglobulin chain of an antibody of the invention; optionally in combination with a polynucleotide of the invention that encodes the variable domain of the other immunoglobulin chain of the antibody of the invention. Preferably, said vector is an expression vector and/or a gene transfer or targeting vector. Expression vectors derived from viruses such as retroviruses, vaccinia virus, adeno-associated virus, herpes viruses, or bovine papilloma virus, may be used for delivery of the polynucleotides or vector of the invention into targeted cell population. Methods which are well known to those skilled in the art can be used to construct recombinant viral vectors; see, for example, the techniques described in Sambrook, Molecular Cloning A Laboratory Manual, Cold Spring Harbor Laboratory (1989) N.Y. and Ausubel, Current Protocols in Molecular Biology, Green Publishing Associates and Wiley Interscience, N.Y. (1994). Alternatively, the polynucleotides and vectors of the invention can be reconstituted into liposomes for delivery to target cells. The vectors containing the polynucleotides of the invention (e.g., the heavy and/or light variable domain(s) of the immunoglobulin chains encoding sequences and expression control sequences) can be transferred into the host cell by well-known methods, which vary depending on the type of cellular host. For example, calcium chloride transfection is commonly utilized for prokaryotic cells, whereas calcium phosphate treatment or electroporation may be used for other cellular hosts; see Sambrook, supra.

The present invention furthermore relates to host cells transformed with a polynucleotide or vector of the invention. Said host cell may be a prokaryotic or eukaryotic cell. The polynucleotide or vector of the invention which is present in the host cell may either be integrated into the genome of the host cell or it may be maintained extrachromosomally. The host cell can be any prokaryotic or eukaryotic cell, such as a bacterial, insect, fungal, plant, animal or human cell. Preferred fungal cells are, for example, those of the genus *Saccharomyces*, in particular those of the species *S. cerevisiae*. The term "prokaryotic" is meant to include all bacteria which can be transformed or transfected with a DNA or RNA molecules for the expression of an antibody of the invention or the corresponding immunoglobulin chains. Prokaryotic hosts may include gram negative as well as gram positive bacteria such as, for example, *E. coli, S. typhimurium, Serratia marcescens* and *Bacillus subtilis*. The term "eukaryotic" is meant to include yeast, higher plant, insect and preferably mammalian cells, most preferably NSO and CHO cells. Depending upon the host employed in a recombinant production procedure, the antibodies or immunoglobulin chains encoded by the polynucleotide of the present invention may be glycosylated or may be non-glycosylated. Antibodies of the invention or the corresponding immunoglobulin chains may also include an initial methionine amino acid residue. A polynucleotide of the invention can be used to transform or transfect the host using any of the techniques commonly known to those of ordinary skill in the art. Furthermore, methods for preparing fused, operably linked genes and expressing them in, e.g., mammalian cells and bacteria are well-known in the art (Sambrook, Molecular Cloning: A Laboratory Manual, Cold Spring Harbor Laboratory, Cold Spring Harbor, N.Y., 1989). The genetic constructs and methods described therein can be utilized for expression of the antibody of the invention or the corresponding immunoglobulin chains in eukaryotic or prokaryotic hosts. In general, expression vectors containing promoter sequences which facilitate the efficient transcription of the inserted polynucleotide are used in connection with the host. The expression vector typically contains an origin of replication, a promoter, and a terminator, as well as specific genes which are capable of providing phenotypic selection of the transformed cells. Suitable source cells for the DNA sequences and host cells for immunoglobulin expression and secretion can be obtained from a number of sources, such as the American Type Culture Collection ("Catalogue of Cell Lines and Hybridomas," Fifth edition (1985) Rockville, Md., U.S.A., which is incorporated herein by reference). Furthermore, transgenic animals, preferably mammals, comprising cells of the invention may be used for the large scale production of the antibody of the invention.

Thus, in a further embodiment, the present invention relates to a method for the production of an antibody capable of inhibiting proliferation of peripheral blood mononuclear cells (PBMCs) or a functional fragment or immunoglobulin chain(s) thereof comprising
(a) culturing the cell of the invention; and
(b) isolating said antibody or functional fragment or immunoglobulin chain(s) thereof from the culture, The transformed hosts can be grown in fermentors and cultured according to techniques known in the art to achieve optimal cell growth. Once expressed, the whole antibodies, their dimers, individual light and heavy chains, or other immunoglobulin forms of the present invention, can be purified according to standard procedures of the art, including ammonium sulfate precipitation, affinity columns, column chromatography, gel electrophoresis and the like; see, Scopes, "Protein Purification", Springer-Verlag, N.Y. (1982). The antibody or its corresponding immunoglobulin chain(s) of the invention can then be isolated from the growth medium, cellular lysates, or cellular membrane fractions. The isolation and purification of the, e.g., microbially expressed antibodies or immunoglobulin chains of the invention may be by any conventional means such as, for example, preparative chromatographic separations and immunological separations such as those involving the use of monoclonal or polyclonal antibodies directed, e.g., against the constant region of the antibody of the invention. It will be apparent to those skilled in the art that the antibodies of the invention can be further coupled to other moieties for, e.g., drug targeting and imaging applications. Such coupling may be conducted chemically after expression of the antibody or antigen to site of attachment or the coupling product may be engineered into the antibody or antigen of the invention at the DNA level. The DNAs are then expressed in a suitable host system, and the expressed proteins are collected and renatured, if necessary.

Substantially pure immunoglobulins of at least about 90 to 95% homogeneity are preferred, and 98 to 99% or more homogeneity most preferred, for pharmaceutical uses. Once purified, partially or to homogeneity as desired, the antibodies may then be used therapeutically (including extracorporeally) or in developing and performing assay procedures.

The present invention also involves a method for producing cells capable of expressing an antibody of the invention or its corresponding immunoglobulin chain(s) comprising genetically engineering cells with the polynucleotide or with the vector of the invention. The cells obtainable by the method of the invention can be used, for example, to test the interaction of the antibody of the invention with its antigen.

Furthermore, the invention relates to an antibody, an immunoglobulin chain thereof and to a binding fragment thereof encoded by a polynucleotide according to the invention or obtainable by the above-described methods or from cells produced by the method described above. The antibodies of the present invention will typically find use individually in treating substantially any disease susceptible to monoclonal antibody-based therapy. In particular, the immunoglobulins can be used as immunosuppressive agents. For an antibody of the invention, typical disease states suitable for treatment include inflammatory symptoms. The antibodies can be used therapeutically in, e.g., patients suffering diseases related to immune response; see supra. Such therapy can be accomplished by, for example, the administration of antibodies, antigens or epitopes of the invention. Such administration can utilize unlabeled as well as labeled antibodies or antigens. Labeling agents can be coupled either directly or indirectly to the antibodies or antigens of the invention. One example of indirect coupling is by use of a spacer moiety. Furthermore, the antibodies of the present invention can comprise a further domain, said domain being linked by covalent or non-covalent bonds. The linkage can be based on genetic fusion according to the methods known in the art and described above or can be performed by, e.g., chemical crosslinking as described in, e.g., WO 94/04686. The additional domain present in the fusion protein comprising the antibody of the invention may preferably be linked by a flexible linker, advantageously a polypeptide linker, wherein said polypeptide linker comprises plural, hydrophilic, peptide-bonded amino acids of a length sufficient to span the distance between the C-terminal end of said further domain and the N-terminal end of the antibody of the invention or vice versa. The above described fusion protein may further comprise a cleavable linker or cleavage site for proteinases. These spacer moieties, in turn, can be either insoluble or soluble (Diener et al., Science, 231:148, 1986) and can be selected to enable drug release from the antigen at the target site. Examples of therapeutic agents which can be coupled to the antibodies, antigens and epitopes of the invention for immunotherapy are drugs, radioisotopes, lectins, and toxins. The drugs with which can be conjugated to the antibodies, antigens and epitopes of the invention include compounds which are classically referred to as drugs such as mitomycin C, daunorubicin, and vinblastine. In using radioisotopically conjugated antibodies, antigens or epitopes of the invention for, e.g., immunotherapy, certain isotopes may be more preferable than others depending on such factors as leukocyte distribution as well as stability and emission. Depending on the autoimmune response, some emitters may be preferable to others. In general, α and β particle-emitting radioisotopes are preferred in immunotherapy. Preferred are short range, high energy emitters such as $^{212}$Bi. Examples of radioisotopes which can be bound to the antibodies, antigens or epitopes of the invention for therapeutic purposes are $^{125}$I, $^{131}$I, $^{90}$Y, $^{67}$Cu, $^{212}$Bi, $^{212}$At, $^{211}$Pb, $^{47}$Sc, $^{109}$Pd and $^{188}$Re. Other therapeutic agents which can be coupled to the antibody, antigen or epitope of the invention, as well as ex vivo and in vivo therapeutic protocols, are known, or can be easily ascertained, by those of ordinary skill in the art. Wherever appropriate the person skilled in the art may use a polynucleotide of the invention encoding any one of the above described antibodies, antigens or the corresponding vectors instead of the proteinaceous material itself.

Moreover, the present invention relates to compositions comprising the aforementioned antibody, antigen or epitope of the invention or chemical derivatives thereof, or the polynucleotide, vector or cell of the invention. The composition of the present invention may further comprise a pharmaceutically acceptable carrier. The term "chemical derivative" describes a molecule that contains additional chemical moieties that are not normally a part of the base molecule. Such moieties may improve the solubility, half-life, absorption, etc. of the base molecule. Alternatively the moieties may attenuate undesirable side effects of the base molecule or decrease the toxicity of the base molecule. Examples of such moieties are described in a variety of texts, such as Remington's Pharmaceutical Sciences. Examples of suitable pharmaceutical carriers are well known in the art and include phosphate buffered saline solutions, water, emulsions, such as oil/water emulsions, various types of wetting agents, sterile solutions etc. Compositions comprising such carriers can be formulated by well-known conventional methods. These pharmaceutical compositions can be administered to the subject at a suitable dose. Administration of the suitable compositions may be effected by different ways, e.g., by intravenous, intraperitoneal, subcutaneous, intramuscular, topical or intradermal administration. Aerosol formulations such as nasal spray formulations include purified aqueous or other solutions of the active agent with preservative agents and isotonic agents. Such formulations are preferably adjusted to a pH and isotonic state compatible with the nasal mucous membranes. Formulations for rectal or vaginal administration may be presented as a suppository with a suitable carrier.

The dosage regimen will be determined by the attending physician and clinical factors. As is well known in the medical arts, dosages for any one patient depend upon many factors, including the patient's size, body surface area, age, the particular compound to be administered, sex, time and route of administration, general health, and other drugs being administered concurrently. A typical dose can be, for example, in the range of 0.001 to 1000 µg (or of nucleic acid for expression or for inhibition of expression in this range); however, doses below or above this exemplary range are envisioned, especially considering the aforementioned factors. Generally, the regimen as a regular administration of the pharmaceutical composition should be in the range of 1 µg to 10 mg units per day. If the regimen is a continuous infusion, it should also be in the range of 1 µg to 10 mg units per kilogram of body weight per minute, respectively. Progress can be monitored by periodic assessment. Dosages will vary but a preferred dosage for intravenous administration of DNA is from approximately $10^6$ to $10^{12}$ copies of the DNA molecule. The compositions of the invention may be administered locally or systemically. Administration will generally be parenterally, e.g., intravenously; DNA may also be administered directly to the target site, e.g., by biolistic delivery to an internal or external target site or by catheter to a site in an artery. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like. Furthermore, the pharmaceutical composition of the invention may comprise further agents such as interleukins or interferons depending on the intended use of the pharmaceutical composition.

In a preferred embodiment, the pharmaceutical composition of the present invention comprises at least one second agent, preferably an agent which inhibits T-cell stimulation depending on the intended use. Such agents include, for example, molecules that are capable of blocking or mimicking receptor/ligand interaction or the like which leads to T-cell suppression. Such agents comprise those blocking the activity of, e.g., costimulatory molecules, such as anti-TIRC7 antibodies, anti-TNF-α antibodies, integrins, Ig-superfamily molecules, selectins as well as drugs blocking chemokines and their respective receptor interactions, drugs blocking IL2/IL2-receptor interaction and other conventional immunosuppressive drugs such as IL-2R mAbs, IL-Toxins and IL-Muteins. Examples for costimulatory molecules and their ligands are described in the prior art, e.g., in Schwartz, Cell 71 (1992), 1065-1068. The interruption of the receptor/ligand interactions by using mAbs or soluble CTLA41g for the interaction between CD28 to the B7-2 and CTLA4 to B7-1 and B7-2 are described in Blazar, J. Immunol. 157 (1996), 3250-3259; Bluestone, Immunity 2 (1995), 555-559; Linsley, Science 257 (1992), 792-95. Examples for blocking the receptor/ligand interaction by using mAbs to CD40 or CD40L are reported by Burden, Nature 381 (1996), 434-435; Kirk, Proc. Natl. Acad. Sci. USA 94 (1997), 8789-8794. CD2 antigen and its ligand LFA-3 are described in Bagogui Li et al., review in Adhesion Molecules, Fusion proteins, Novel Peptides, and Monoclonal Antibodies, Recent Developments in Transplantation Medicine, Vol. II, 1995, Physicians & Scientists Publishing Co., Inc. and blocking of their interaction by using of mAbs (anti-Leu-5b, OKT11, T11) is reported in Bromberg, Transplantation 51 (1991) 219-225 or CD2.1gG1 fusion protein. The use of monoclonal Abs agains CD4 molecule is described in Cosimi, Surgery 108 (1990), 406-414. CD47 blockade by mAbs is described by Rheinhold, J. Exp. Med. 185 (1997), 1-11. Integrins and Ig-superfamily molecules include LFA-1 with its ligand ICAM-1, -2, -3, Mac-1 with its ligand ICAM-1, -3; ICAM-1 with its ligand LFA-1, Mac-1, CD43; ICAM-2 with its ligand LFA-1; ICAM-3 with its ligand LFA-1, Mac-1; $V_L A4$ and VCAM-1 see, e.g., David, Adams, review in Adhesion Molecules, Fusion proteins, Novel Peptides, and Monoclonal Antibodies, Recent Developments in Transplantation Medicine, Vol. II, 1995, Physicians & Scientists Publishing Co., Inc.; Isobe, Science, 255 (1992), 1125-1127; Cosimi, J. Immunology 144 (1990), 4604-4612; Hynes, Cell 69 (1992), 11-25.

Furthermore selectively interfering agents with $V_L A$-4 mAbs to the alpha4 integrin chain (CD49d) can be used, beta1 integrin chain (CD29), or an activation-induced neo-epitope of $V_L A$-4 as well as soluble $V_L A$-4 ligands such as soluble fibronectin or its relevant peptide (GPEILDVPST), or soluble VCAM-1 or its relevant peptide. More selectively blocking agents are antisense oligonucleotides, designed to selectively hybridize with cytoplasmic alpha4, beta1, or VCAM-1 mRNA; Fedoseyeva, J. Immunol. 57 (1994), 606-612. Another example is the drug pentoxilylline (PTX) that is able to block expression of VCAM-1; Besler, J. Leukoc. Biol. 40 (1986), 747-754. Furthermore, VCAM-1 mAb, M/K-2, antimurine, for example could prolong allograft survival, Orosz, Transplantation, 56 (1993), 453-460. Blocking of members of the integrin family and their ligands by using mAbs is described in Kupiec-Weglinski, review in Adhesion Molecules, Fusion proteins, Novel Peptides, and Monoclonal Antibodies, Recent Developments in Transplantation Medicine, Vol. II, 1995, Physicians & Scientists Publishing Co., Inc. Selectins, e.g., L-selectin (CD62L), E-selectin (CD62E), P-selectin (CD62P) have been described in Forrest and Paulson, Selectin family of adhesion molecules. In: Granger and Schmid-Schonbein, eds. Physiology and Pathophysiology of Leukocyte Adhesion. New York, Oxford Press, 1995, pp 68-146. The combination of conventional immunosuppressive drugs, e.g., ATG, ALG, OKT3, Azathioprine, Mycophenylate, Mofetyl, Cyclosporin A, FK506, Sirolimus (Rapamune), Corticosteroids may be used as described in Cosimi, Transplantation 32 (1981), 535-539; Shield, Transplantation 38 (1984), 695-701, and Graft, June 2001, Vol 4 (4). The interruption of chemokines and interactions with their respective receptor by using mAbs is reviewed in Luster, Chemokines-chemotactic cytokines that mediate inflammation, New Engl. J. Med. February (1998), 436-445. Thus, any agent as defined above and referenced by way of example can be used in accordance with the pharmaceutical composition of the invention or the methods and uses described herein.

Furthermore, the pharmaceutical composition may also be formulated as a vaccine, for example, if the pharmaceutical composition of the invention comprises an antigen as described above that is capable of eliciting an effective immune response against TIRC7. Advantageously, the pharmaceutical composition of the invention is intended for use in organ transplantation.

Therapeutic or diagnostic compositions of the invention are administered to an individual in a therapeutically effective dose sufficient to treat or diagnose disorders in which modulation of TIRC7-related activity is indicated. The effective amount may vary according to a variety of factors such as the individual's condition, weight, sex and age. Other factors include the mode of administration. The pharmaceutical compositions may be provided to the individuals by a variety of routes such as by intracoronary, intraperitoneal, subcutaneous, intravenous, transdermal, intrasynovial, intramuscular or oral routes. In addition, co-administration or sequential administration of other agents may be desirable.

A therapeutically effective dose refers to that amount of antibodies, antigens, polynucleotides and vectors of the invention to ameliorate the symptoms or condition. Therapeutic efficacy and toxicity of such compounds can be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50.

Thus, the present invention relates to the use of the antibody and the antigen of the invention for the preparation of a pharmaceutical composition for inhibition of an immune response, preferably for the treatment of graft versus host disease, autoimmune diseases, allergic diseases, infectious diseases, sepsis, for the treatment of tumors, for the improvement of wound healing or for inducing or maintaining immune unresponsiveness in a subject; see also supra.

Accordingly, the present invention also relates to a method of modulating the immune response in a subject in need thereof, comprising administering the antibody or the antigen of the invention. Compositions comprising the antibody or the antigen of this invention can be added to cells in culture (in vitro) or used to treat patients, such as mammals (in vivo). Where the antibody or the antigen are used to treat a patient, the polypeptide is preferably combined in a pharmaceutical composition with a pharmaceutically acceptable carrier such as a larger molecule to promote polypeptide stability or a pharmaceutically acceptable buffer that serves as a carrier for the antibodies that has more than one antibody coupled to a single entity. The methods of the invention include administering to a patient, preferably a mammal, and more preferably a human, the composition of the invention in an amount effective to produce the desired effect. The antibody or the antigen can be administered as a single dose or in multiple doses. Useful dosages of the active agents can be determined by comparing their in vitro activity and the in vivo activity in animal models. Methods for extrapolation of effective dosages in mice, and other animals, to humans are known in the art. The present invention also provides a method of modulating (e.g., activating or inhibiting) immune cell (e.g., T-cells, B-cells, NK cells, LAK cells, or dendritic cells) activation, proliferation, and/or differentiation that includes contacting an immune cell with an antibody or the antigen described above.

From the foregoing, it is evident that the present invention encompasses any use of a ligand binding molecule comprising at least one CDR of the above described antibody, in particular for diagnosing and/or treatment of a disorder related to the aberrant expression or malfunction of T-cell immune response cDNA 7 (TIRC7). Preferably, said ligand binding molecule is an antibody of the present invention or an immunoglobulin chain thereof.

The biological activity of the antibodies identified here suggests that they have sufficient affinity to make them potential candidates for drug localization to cells expressing the appropriate surface structures. This targeting and binding to cells could be useful for the delivery of therapeutically active agents (including targeting drugs, DNA sequences, RNA sequences, lipids, proteins (e.g., human growth factors)) and gene therapy/gene delivery. More preferably, the therapeutically active agent is an anti-inflammatory agent.

Molecules/particles with an anti-TIRC7 antibody would bind specifically to cells/tissues expressing TIRC7, and therefore could have diagnostic and therapeutic use. Thus, the antibody or the antigen of the present invention can be labeled (e.g., fluorescent, radioactive, enzyme, nuclear magnetic) and used to detect specific targets in vivo or in vitro including "immunochemistry" like assays in vitro. In vivo they could be used in a manner similar to nuclear medicine imaging techniques to detect tissues, cells, or other material expressing TIRC7. Another method involves delivering a therapeutically active agent to a patient. The method includes administering at least one antibody or the antigen and the therapeutically active agent to a patient. Preferably, the therapeutically active agent is selected from drugs, DNA sequences, RNA sequences, proteins, lipids, and combinations thereof. More preferably, the therapeutically active agent is an antibacterial agent, anti-inflammatory agent, or antineoplastic agent.

In another embodiment the present invention relates to a diagnostic composition comprising any one of the above described the antibodies, antigens, polynucleotides, vectors or cells of the invention and optionally suitable means for detection. The antigens and antibodies of the invention are, for example, suited for use in immunoassays in which they can be utilized in liquid phase or bound to a solid phase carrier. Examples of immunoassays which can utilize the antigen of the invention are competitive and non-competitive immunoassays in either a direct or indirect format. Examples of such immunoassays are the radioimmunoassay (RIA), the sandwich (immunometric assay) and the Western blot assay. The antigens and antibodies of the invention can be bound to many different carriers and used to isolate cells specifically bound to said polypeptides. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for the purposes of the invention. There are many different labels and methods of labeling known to those of ordinary skill in the art. Examples of the types of labels which can be used in the present invention include enzymes, radioisotopes, colloidal metals, fluorescent compounds, chemiluminescent compounds, and bioluminescent compounds; see also the embodiments discussed hereinabove.

By a further embodiment, the antibodies of the invention may also be used in a method for the diagnosis of TIRC7 related diseases in an individual by obtaining a body fluid sample from the tested individual which may be a blood sample, a lymph sample or any other body fluid sample and contacting the body fluid sample with an antibody of the invention under conditions enabling the formation of antibody-antigen complexes. The level of such complexes is then determined by methods known in the art, a level significantly higher than that formed in a control sample indicating the disease in the tested individual. In the same manner, the specific antigen bound by the antibodies of the invention may also be used. Thus, the present invention relates to an in vitro immunoassay comprising the antibody or the antigen of the invention.

Furthermore, the present invention relates to an oligonucleotide comprising a nucleotide sequence of any one of SEQ ID NOs: 12 to 40 and their use for the cloning of an anti-TIRC7 antibody; see the appended examples.

These and other embodiments are disclosed and encompassed by the description and Examples of the present invention. Further literature concerning any one of the antibodies, methods, uses and compounds to be employed in accordance with the present invention may be retrieved from public libraries and databases, using for example electronic devices. For example the public database "Medline" may be utilized, which is hosted by the National Center for Biotechnology Information and/or the National Library of Medicine at the National Institutes of Health. Further databases and web addresses, such as those of the European Bioinformatics Institute (EBI), which is part of the European Molecular Biology Laboratory (EMBL) are known to the person skilled in the art and can also be obtained using internet search engines. An overview of patent information in biotechnology and a survey of relevant sources of patent information useful for retrospective searching and for current awareness is given in Berks, TIBTECH 12 (1994), 352-364.

The above disclosure generally describes the present invention. A more complete understanding can be obtained by reference to the following specific examples which are provided herein for purposes of illustration only and are not intended to limit the scope of the invention.

The Figures show:

FIG. 1: Functional assays in the presence of TIRC7 antibodies; see Example 1.

Figure 2:
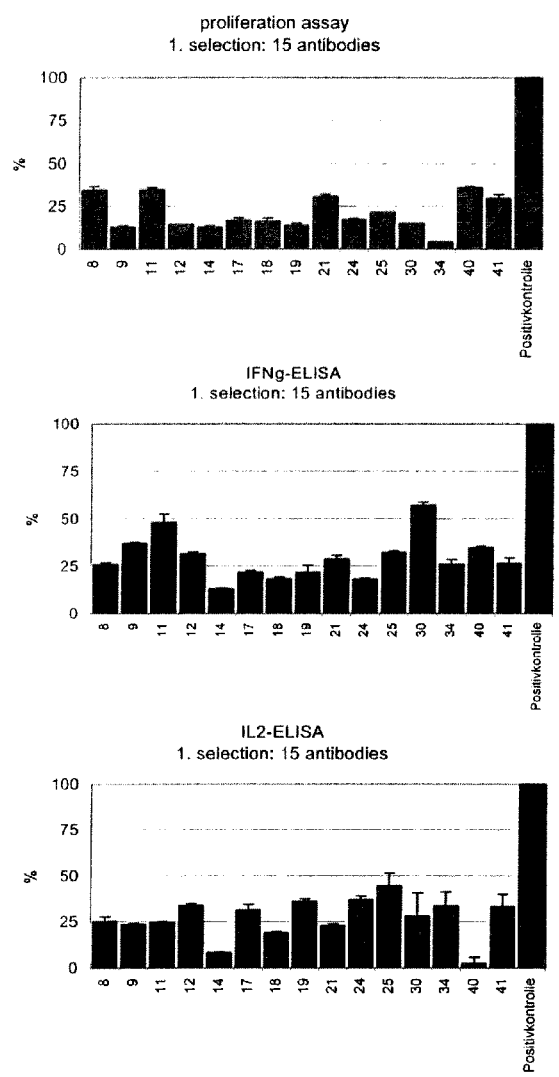

FIG. 2: Functional assays in the presence of 15 selected TIRC7 mAbs; see Example 1.

Figure 3:
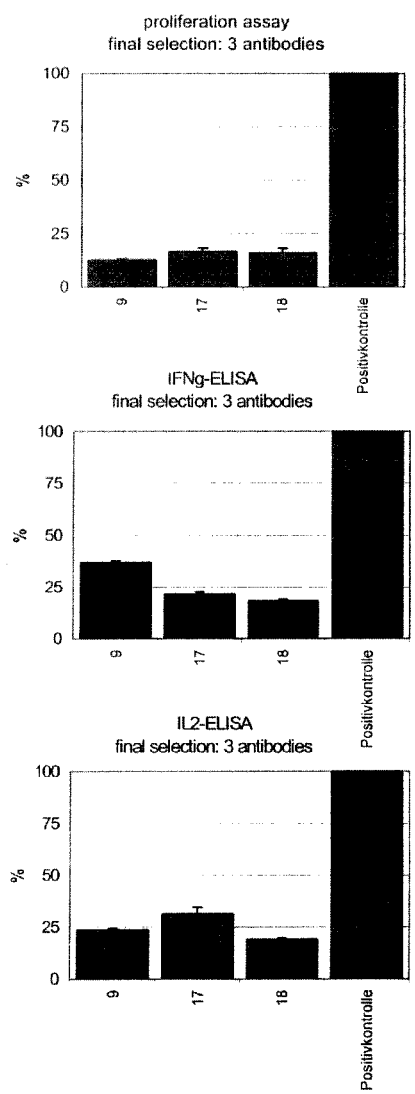

FIG. 3: Functional assays in the presence of three selected therapeutic TIRC7 mAbs; see Example 1 and Table 1.

FIG. 4: $V_H$ sequence of clone 9 (Metiliximab) (CDRs are underlined) the amino acid sequence of which is represented by SEQ ID NO:2.

FIG. 5: $V_L$ sequence of clone 9 (Metiliximab) (CDRs are underlined) the amino acid sequence of which is represented by SEQ ID NO:4.

FIG. 6: $V_H$ sequence of clone 17-1 (Neliximab) (CDRs are underlined) the amino acid sequence of which is represented by SEQ ID NO:6.

FIG. 7: $V_L$ sequence of clone 17-1 (Neliximab) (CDRs are underlined) the amino acid sequence of which is represented by SEQ ID NO:8.

Figure 8:
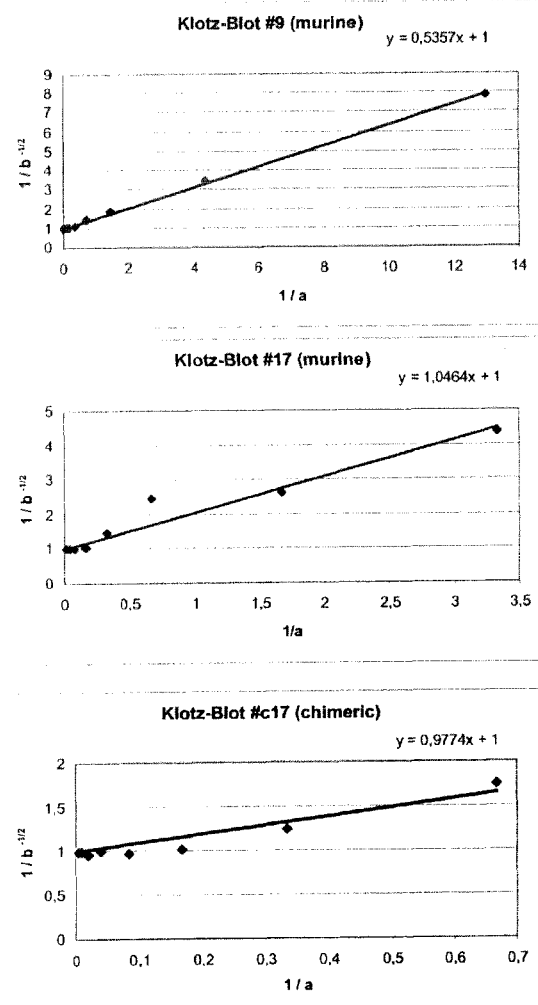

FIG. 8: Affinity measurement of monoclonal antibodies: 1. Affinity measurement of murine and chimeric antibodies against Vol 6 had been done by the method of Friquet et al 1985. Thereby, the antibody (in nM concentration) had been titrated with increasing concentrations of Vol 6 until equilibrium had been reached. The fraction of free antibody had been determined by ELISA. Symbols of the Klotz-Blot representation: a=antigen concentration (peptide 6) in nM, b=bound antibody. Bivalency of the antibodies had been considered by blotting $b^{-1/2}$ against 1/a.

Figure 9:
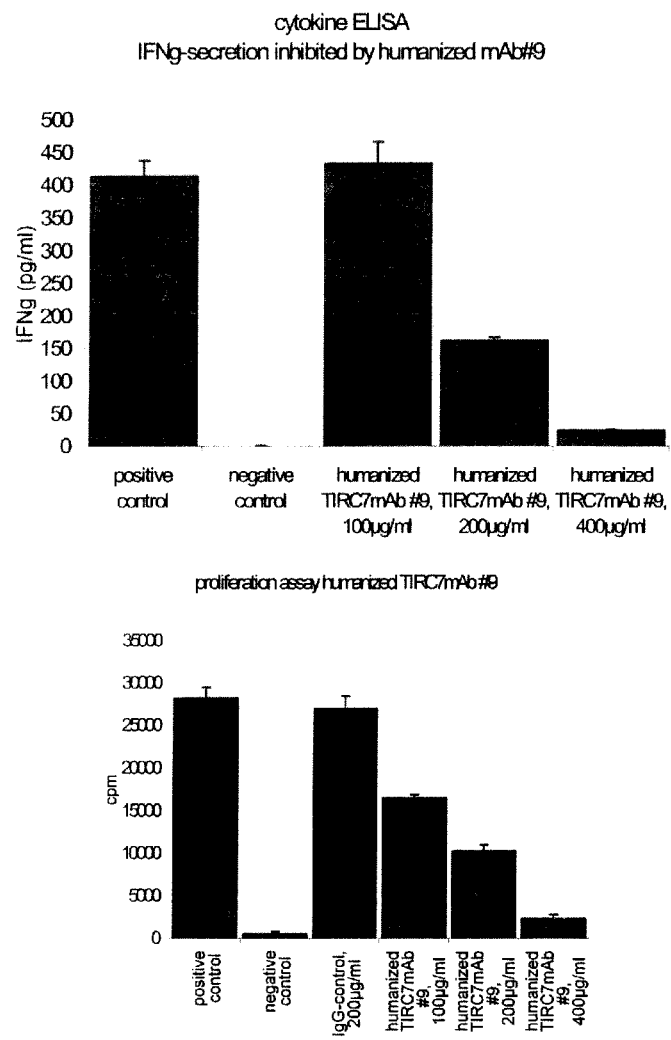

FIG. 9: Functional assays in the presence of chimerized (termed humanized in FIG. 9 because of their human constant region, but chimerized is meant) therapeutic TIRC7 mAb. Shown is the functional capacity of inhibition of the chimerized anti-TIRC7 mAb antibody on T cell proliferation (proliferation assay) as well as IFN-gamma cytokine inhibition (cytokine ELISA) after 48 h activation of human T cells in the presence of mitogen in a dose dependent manner.

The examples illustrate the invention.

EXAMPLE 1

Generation and Selection of Monoclonal Antibodies Directed Against TIRC7

Balb/c-mice were immunized in presence of Freunds adjuvans with one of six peptides derived from the sequence of several hypothetically extracellular domains of TIRC7. Priming of mice with antigen was followed by several booster injections over a period of 3 months. Fusion of spleen cells with SP2/0-Ag14 myeloma cells was carried out according to the PEG-fusion technique. All together 15 fusions were performed and pursued successfully. After 3 weeks of selection in HAT-media, repeated separation of the cells according to the limiting-dilution method and screening of the supernatants using the ELISA technique 192 stable antibody producing hybribodomas were received. Determination of the antibody isotype revealed that 140 of 192 monoclonal antibodies were IgM antibodies whereas 52 were IgG antibodies. All 52 IgG antibody producing hybridomas were thawed, separated once more and tested regarding their IgG-production. Hybridomas which produced less than 5 µg IgG per ml supernatant after cell death were excluded.

42 antibodies were produced in small volumes of 150-200 ml supernatant and purified using protein A or protein G on a HPLC affinity chromatographic column. Purified antibodies were tested regarding their capacity to inhibit immune response to mitogens (FIG. 1, proliferation assay) as well as their effects on cytokine expression in the supernatants of 48 hours activated human cells (FIG. 1, IFNg and hIL 2 ELISA).
Radioactive Proliferation Assay—Incorporation of $^3$H-Thymidine:

PBMC of healthy donors were isolated according to the Ficoll-Paque density centrifugation protocol. Samples of 50000 PBMC's/well were stimulated with PHA (1 µg/ml) and incubated for 48 h at 5% $CO_2$, 37° C. in presence of TIRC7-antibodies and IgG-control antibodies in a total volume of 100 µl/well. Samples were run in triplicates on 96 well-microtiter-plates (MTPs). After 48 h 0.5 µCi$^3$H-thymidine per well were added and the cells were reincubated for additional 18 hours. Cells were harvested and lysed using a cell harvester and collected on nitrocellulose-filter-MTP's. Plates were dried at room temperature for 4 hours. To enhance the radioactive signal produced by the samples a scintillation fluid was added and counts per minute (cpm) were measured with a beta counter.
Quantitation of Secreted Cytokines in PBMC-Supernatants:

PBMC of healthy donors were isolated according to the Ficoll-Paque density centrifugation protocol. Samples of 50000 PBMCs/well were stimulated with PHA (1 µg/ml) and incubated for 48 hours at 5% $CO_2$, 37° C. in presence of TIRC7-antibodies and IgG-control antibodies in a total volume of 100 µl/well. Samples were run in triplicates on 96 well-microtiter-plates (MTPs). After 48 hours MTPs were centrifuged at 300×g for 10 minutes and supernatants collected from the wells. The quantitation of cytokines in the supernatant was carried out on anti-cytokine-antibody-coated microtiter strips provided with the Cytoscreen® ELISA Kit, Biosource. The formerly collected supernatants and diluted standards were incubated in presence of a biotinylated secondary antibody recognizing the specific cytokine for 1.5-3 hours at room temperature on these strips depending on the determined cytokine. Afterwards excessive secondary antibody was removed by washing 3 times with washing buffer. A streptavidin-peroxidase conjugate was added and incubated for 45 minutes-1 hour at room temperature. Excessive conjugate was removed by washing. TMB-substrate-solution was added and the strips incubated for additional 30 minutes in the dark followed by the addition of stop solution. The colour development was measured at 450 nm and the numbers were statistically analyzed.

The first functional screen led to 15 antibodies which inhibited the proliferation (FIG. 2, proliferation assay) as well as the secretion of IFNγ and IL-2 (FIG. 2) of PHA-stimulated human PBMC of healthy donors below 30% calculated in relation to the positive control (100%).

The next selection process was performed based on production stability of the hybridoma, stability of the antibody, immunoprecipitating qualities and immunofluorescence staining. Finally three antibodies were selected, #9 and #17, both descended from fusions performed with spleen cells of mice that had been immunized with peptides derived from the largest extracellular loop of TIRC7, and #18, in this case the peptide used for immunization was derived from the extracellular C-Terminus of TIRC7 (FIG. 3). The following table shows the IgG-Isotype and peptide used for immunization for the selected 3 antibodies:

TABLE 1

| Isotype determination | | |
|---|---|---|
| antibody | Isotype | Peptide |
| #9 | IgG1,κ | Peptide6 |
| #17 | IgG1,κ | Peptide7c |
| #18 | IgG2b,κ | Peptide4 |

These antibodies have been further investigated. Furthermore, the antibody of Clone 9 has been designated Metiliximab and that of Clone 17 has been designated Neliximab.

EXAMPLE 2

Development of Chimeric Antibodies

1. Identification of the $V_H$ and $V_L$ Regions of the Antibodies Metiliximab and Neliximab 1.1. RNA isolation. As a RNA source hybridoma cells were used expressing the antibodies described in Example 1, supra. Isolation was done with the RNA isolation columns of QIAGEN (Mini) according to the manufactor's instructions.

1.2. cDNA synthesis. cDNA-synthesis was done with total RNA: 3 µg total RNA in 170 volume was incubated with 2 µl cDNA-Primer mentioned in Table 2 and incubated for 10 minutes at 75° C.

TABLE 2

Primer sequences for cDNA-synthesis and amplification of murine variable regions ($V_H$ and $V_L$)

A: primer for cDNA-synthesis:

of the $V_H$ regions

MOCG12Forcor: CAC AAT TTT CTT GTC CAC CTT GGT GC (SEQ ID NO: 41)

of the $V_L$ regions

MOCKFOR: CTC ATT CCT GTT GAA GCT CTT GAC AAT (SEQ ID NO: 42)

B: primer for amplification of murine variable regions $V_H$ chain:
Back primer

| Name | Sequence |
|---|---|
| MHV.B1.NCoI | GAA TAG GCC ATG GCG GAT GTG AAG CTG CAG GAG TC (SEQ ID NO: 40) |
| MHV.B2.NCoI | GAA TAG GCC ATG GCG CAG GTG CAG CTG AAG GAG TC (SEQ ID NO: 13) |
| MHV.B3.NCoI | GAA TAG GCC ATG GCG CAG GTG CAG CTG AAG CAG TC (SEQ ID NO: 14) |
| MHV.B4.NCoI | GAA TAG GCC ATG GCG CAG GTT ACT CTG AAA GAG TC (SEQ ID NO: 15) |
| MHV.B5.NCoI | GAA TAG GCC ATG GCG GAG GTC CAG CTG CAA CAA TCT (SEQ ID NO: 16) |
| MHV.B6.NCoI | GAA TAG GCC ATG GCG GAG GTC CAG CTG CAG CAG TC (SEQ ID NO: 17) |
| MHV.B7.NCoI | GAA TAG GCC ATG GCG CAG GTC CAA CTG CAG CAG CCT (SEQ ID NO: 18) |
| MHV.B8.NCoI | GAA TAG GCC ATG GCG GAG GTG AAC CTG GTG GAG TC (SEQ ID NO: 19) |
| MHV.B9.NCoI | GAA TAG GCC ATG GCG GAG GTG AAG CTG GTG GAA TC (SEQ ID NO: 20) |
| MHV.B10.NCoI | GAA TAG GCC ATG GCG GAT GTG AAC TTG GAA GTG TC (SEQ ID NO: 21) |
| MHV.B11.NCoI | GAA TAG GCC ATG GCG GAG GTC CAG CTG CAA CAG TC (SEQ ID NO: 22) |
| MHV.B12.NCoI | GAA TAG GCC ATG GCG GAG GTG CAG CTG GAG GAG TC (SEQ ID NO: 23) |

Forward primer

| Name | Sequence |
|---|---|
| MHC.F.HindIII | GGC CAG TGG ATA AAC CTT GGG GGT GTC GTT TTG GC (SEQ ID NO: 24) |

$V_L$-chain:
Back primer

| Name | Sequence |
|---|---|
| MKV.B1.MluI | TAC AGG ATC CAC GCG TAG ATG TTT TGA TGA CCC AAA CT (SEQ ID NO: 25) |
| MKV.B2.MluI | TAC AGG ATC CAC GCG TAG ATA TTG TGA TGA CGC AGG CT (SEQ ID NO: 26) |
| MKV.B3.MluI | TAC AGG ATC CAC GCG TAG ATA TTG TGA TAA CCC AG (SEQ ID NO: 27) |
| MKV.B4.MluI | TAC AGG ATC CAC GCG TAG ACA TTG TGC TGA CCC AAT CT (SEQ ID NO: 28) |
| MKV.B5.MluI | TAC AGG ATC CAC GCG TAG ACA TTG TGA TGA CCC AGT CT (SEQ ID NO: 29) |

TABLE 2-continued

Primer sequences for cDNA-synthesis and amplification of murine variable regions (V$_H$ and V$_L$)

| | |
|---|---|
| MKV.B6.MluI | TAC AGG ATC CAC GCG TAG ATA TTG TGC TAA CTC AGT CT (SEQ ID NO: 30) |
| MKV.B7.MluI | TAC AGG ATC CAC GCG TAG ATA TCC AGA TGA CAC AGA CT (SEQ ID NO: 31) |
| MKV.B8.MluI | TAC AGG ATC CAC GCG TAG ACA TCC AGC TGA CTC AGT CT (SEQ ID NO: 32) |
| MKV.B9.MluI | TAC AGG ATC CAC GCG TAC AAA TTG TTC TCA CCC AGT CT (SEQ ID NO: 33) |
| MKV.B10.MluI | TAC AGG ATC CAC GCG TAG ACA TTC TGA TGA CCC AGT CT (SEQ ID NO: 34) |
| Forward primer | |
| MKV.F.Not | TGA CAA GCT TGC GGC CGC GGA TAC AGT TGG TGC AGC ATC (SEQ ID NO: 35) |

A mix consisting of 8 µl First-strand-buffer, 4 µl DTT, 4 µl dNTP, 0.5 µl RnaseInhibitor and 1 µl Dnase was added and further incubated for 30 minutes at 37° C. Enzymes were deactivated by incubation in 75° C. for 5 minutes. 1 µl reverse transcriptase and 1 µl RnaseInhibitor was added and cDNA was synthesized by incubation with 42° C. for 45 minutes. Heat inactivation occurred at 94° C. for 5 minutes.

1.3. PCR-amplification of the variable regions. Amplification was done with the components of the CLONTECH Advantage-high-fidelity Polymerase. The reaction occurred in 50 µl volume with 1 µl of the cDNA (200 pg), 5 µl reaction-buffer, 200 µM of an equimolar mix of dNTP and 25 pmol of the Forward Primer and 25 pmol Backprimer mentioned in Table 2. Amplification was done with 36 Cycles, each with denaturation at 94° C. for 15 seconds, annealing at 55° C. to 65° C. for 30 seconds and elongation for 30 seconds at 72° C. After the last amplification cycle, one additional elongation for 5 minutes was added.

1.4. Cloning of the PCR amplified V-regions into the procaryotic expression vector pOPE-101 (Genbank# Y14585). PCR products, which were amplified with the different annealing temperatures were pooled and DNA was precipitated by the addition of sodiumacetate pH 5.2 (1/10 volume), ethanol (2.5 volume) and 1 µl glycogen (ROCHE) as a carrier. DNA was purified on an 1% agarose gel, excised (QIAGEN Gel purification kit) and either NotI/MluI (New England Biolabs) digested for the V$_L$ region or NcoI/Hind III (New England Biolabs) for the V$_H$ region. Digestion occurred in 50 µl reaction volume with 45 µl purified DNA (about 2 µg), 5 µl recommended buffer and 5 units of enzyme for 3 hours at 37° C.

Digested DNA was purified by running on a 1% agarose gel and excised from the gel according to the manufactures instructions (QIAGEN Gel purification kit). A 50 ng portion of the digested and gel-purified V$_L$ region was ligated with 500 ng of the appropriately digested and purified expression vector pOPE101 in a final volume of 40 µl with 1 µl ligase (Boeringer Mannheim) at 16° C. overnight. DNA was precipitated, electroporated in XL 1 blue (Epicurian coli; STRATAGENE), and bacteria were grown for 1 h in 1 ml SOC-medium to allow recuperation. Bacteria were plated on SOB$_{GAT}$ plates (0.1 M glucose, 100 µgml$^{-1}$ ampicillin, 12.5 µgml$^{-1}$, tetracycline), and, after overnight incubation, clones were scraped off and DNA was isolated with a DNA purification column according to the manufacturer's instructions (MACHEREY and NAGEL).

Vector DNA (containing the V$_L$ chain) was digested with NcoI/HindIII, purified by running on a 1% agarose gel and excised from the gel according to the manufacturer's instructions (QIAGEN Gel purification kit).

Ligation of this purified and digested vector DNA with the NcoI/HindIII digested V$_H$-regions mentioned above was done as described. After electroporation in E. coli independent clones were picked and screened for the expression of functional scFv (single-chains) with specificity against Peptide.

1.5. Screening of the transfected bacteria for positive binders. Bacterial expression was IPTG-induced and soluble scFv-myc fusion protein was rescued from the periplasmatic compartment by osmotic lysis of the bacteria. Supernatant containing the scFv-myc fusion protein was blocked in 2% Milk PBS and incubated for 3 h in wells of an ELISA-Plate previously coated with 100 ng peptide/well. Detection of Peptid6-bound scFv was done by incubation with anti-c-myc (mouse) and Horseradish-peroxidase conjugated anti-mouse (rabbit). Vector DNA of positive clones were rescued and the V$_H$ and V$_L$ regions nucleotide sequences were determined. Sequences of the V$_H$ and V$_L$ regions are depicted in FIGS. 4 to 7.

2. Construction of the Chimeric Antibodies

For the construction of the chimeric recombinant antibodies, the V$_H$ and V$_L$ variable regions were either cloned into the pConGamma1f-vector (for the V$_H$ region) or into the pConKappa-vector (for the V$_L$ region) purchased by LONZA Biologics, (Slough, UK). Thereby, upstream of the variable regions a IgG-leader sequence and a Kozak-sequence was introduced for secretion into the medium. The two vectors (pConGamm1f and pConKappa) had been fused in order to facilitate transfection and to achieve a balanced production of light and heavy chains.

2.1. Introduction of the eukaryotic leader sequence by PCR: components of the CLONTECH Advantage-high-fidelity Polymerase had been used. The PCR reaction occurred in 50 µl volume with 1 µl (100 ng) of the pOPE vector containing either the V$_H$ or the V$_L$ region as a template, 5 µl reaction-buffer, 200 µM of an equimolar mix of dNTP and 25 pmol of the Forward Primer and 25 pmol Backprimer mentioned in Table 3.

TABLE 3

Primer for the introduction of the leadersequence and cloning of the V-regions:

cloning of the V<sub>H</sub> chain in the pConGamma1f Vector:

5'-primer:
5' #9Leader V<sub>H</sub>-HindIII: 5'-GCG CGC AAG CTT GCC GCC ACC ATG GGA TGG
AGC TGT ATC ATC CTC TTC TTG GTA GCA ACA GCT ACA
GGT GTC CAC TCC GAG GTG CAG CTG CAA CAG TC-3'
(SEQ ID NO: 36)

3'-primer:
3'#9VH-ApaI: 5'-TTT ATA TGG GCC CTT GGT GGA GGC TGA GGA GAC
GGT GAC CGT GGT-3' (SEQ ID NO: 37)

cloning of the V.sub.H-chain in the pConKappa Vector:

5'-primer:
5' #9Leader V<sub>L</sub>-HindIII: 5'-GCG CGC AAG CTT GCC GCC ACC ATG GGA
TGG AGC TGT ATC ATC CTC TTC TTG GTA GCA
ACA GCT ACA GGT GTC CAC TCC CAA ATT GTT
CTC ACC CAG TCT -3' (SEQ ID NO: 38)

3'-primer:
3' #9V<sub>L</sub>-BsiWI: 5'-ATA TGG CGT ACG TTT GAT TTC CAA CTT GGT GCC (SEQ ID NO: 39)

auxilliary primer for the 5' primer:

HindIII-Kozakbeg: 5'-GCG CGC AAG CTT GCC GCC AC -3' (SEQ ID NO: 12)

Amplification was done with 36 Cycles, each with denaturation at 94° C. for 15 seconds, annealing at 65° C. for 30 seconds and elongation for 30 seconds at 72° C. After the 10$^{th}$ cycle, 25 pmol of the primer HindIII-Kozakbeg (see Table 3) had been added to the reaction mix. After the last amplification cycle, one additional elongation period for 5 minutes was added.

2.2. Cloning into vectors containing the IgG-constant region. The PCR product was purified by running on a 1% agarose gel, digested with HindIII/ApaI (V<sub>H</sub> chain) or Hind III/BsiWI (V<sub>L</sub> chain) and again gel purified. 50 ng of the digested V<sub>H</sub> and V<sub>L</sub> regions were ligated into 200 ng of the appropriately digested pConGamma1f and pConKappa vectors, respectively. The V<sub>H</sub> expression cassette, containing the promoter-region and the gene for the entire Heavy chain, was rescued from the pConGamma1f-vector by digestion with NotI/SalI and ligated in the appropriately digested and purified pConKappa vector. The resulted double gene vector was linearized with Pvu I, phenol/chloroform extracted and 1 μg was used for the transfection of either 1×10$^7$ NSO or CHO cells.

Antibody was isolated and tested for binding and biological activity. The binding and functional characteristics of the chimeric antibodies as compared to the murine antibodies are shown in FIGS. 8 and 9, and can be summarized as follows:
ELISA: -Specificity for the TIRC7 derived peptide Peptid6
WesternBlot: -Same band pattern as the murine mAb
T cell proliferation assay: -Inhibition of mitogen induced T cell proliferation
Affinity measurement: -Affinity of chimeric Neliximab against peptide6: Kd=1 nM
  Affinity of murine Neliximab against peptide6: Kd=1 nM
  Affinity of murine Metiliximab against peptide6: Kd=0.5 nM
  Affinity of chimeric Neliximab against peptide6: Kd=1 nM The complete disclosure of all patents, patent documents, and publications cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention claimed by the claims.

The invention claimed is:

1. A monoclonal antibody or antigen binding fragment thereof that is capable of binding to an antigen comprising or consisting of the amino acid sequence of SEQ ID NO:9, comprising all three complementarity determining regions (CDR) of the $V_H$ variable region, and all three complementarity determining regions (CDR) of the $V_L$ variable region, wherein the amino acid sequences of said $V_H$ variable region and said $V_L$ variable region comprise the amino acid sequences set forth in SEQ ID NO: 2 ($V_H$) and SEQ ID NO: 4 ($V_L$), respectively.

2. The antibody of claim 1, wherein said antibody is a chimeric or humanized antibody.

3. The antibody of claim 1 comprising the amino acid sequence of the $V_H$ and/or $V_L$ region as depicted in any one of FIG. 4 or 5.

4. A polynucleotide encoding at least a variable region of an immunoglobulin chain of the antibody of claim 1.

5. A vector comprising the polynucleotide of claim 4.

6. A host cell comprising a polynucleotide of claim 4.

7. A method for preparing an antibody or a functional fragment or immunoglobulin chain(s) thereof comprising (a) culturing the cell of claim 6; and
(b) isolating said antibody or functional fragment or immunoglobulin chain(s) thereof from the culture.

8. An antibody, an immunoglobulin chain thereof or an antigen binding fragment thereof encoded by a polynucleotide of claim 4.

9. A composition comprising the antibody of claim 1.

10. The composition of claim 9 which is a pharmaceutical composition and further comprises a pharmaceutically acceptable carrier.

11. A diagnostic composition comprising the antibody of claim 1 coupled to a detectable label.

12. An antibody or an antigen binding fragment thereof obtainable by a method comprising:

(a) culturing a host cell comprising a polynucleotide encoding the $V_H$ and the $V_L$ variable region which are set forth in SEQ ID NO:2 and SEQ ID NO:4, respectively, and
(b) isolating said antibody or antigen binding fragment thereof from the culture.

* * * * *